(12) United States Patent
Wang et al.

(10) Patent No.: US 10,941,412 B2
(45) Date of Patent: Mar. 9, 2021

(54) **CITRUS VARIETIES RESISTANT TO *XANTHOMONAS CITRI* INFECTION**

(71) Applicant: UNIVERSITY OF FLORIDA RESEARCH FOUNDATION, INCORPORATED, Gainesville, FL (US)

(72) Inventors: Nian Wang, Auburndale, FL (US); Hongge Jia, Winter Haven, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/439,144

(22) Filed: Jun. 12, 2019

(65) Prior Publication Data
US 2019/0367941 A1 Dec. 5, 2019

Related U.S. Application Data

(62) Division of application No. 15/757,377, filed as application No. PCT/US2016/049878 on Sep. 1, 2016.

(60) Provisional application No. 62/214,623, filed on Sep. 4, 2015.

(51) Int. Cl.
C12N 15/82 (2006.01)
C12N 15/11 (2006.01)

(52) U.S. Cl.
CPC .......... *C12N 15/8281* (2013.01); *C12N 15/11* (2013.01); *C12N 15/8213* (2013.01); *C12N 15/8239* (2013.01); *C12N 2310/20* (2017.05)

(58) Field of Classification Search
None
See application file for complete search history.

Primary Examiner — Brent T Page
(74) Attorney, Agent, or Firm — Timothy H. Van Dyke; Wolter Van Dyke; Davis, PLLC

(57) ABSTRACT

The invention pertains to a plant cell or a plant having one or more mutations in the promoters of both the alleles for CsLOB1 gene, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of the CsLOB1 genes. Also, a plant cell or a plant having one or more mutations in the coding regions of both the alleles for CsLOB1 gene, wherein the one or more mutations reduce or abolish the binding of the function of CsLOB1 protein are provided. The invention further pertains to the methods of making the plant cell or the plant resistant to infection by *Xanthomonas* spp.

7 Claims, 25 Drawing Sheets
Specification includes a Sequence Listing.

| | | |
|---|---|---|
| Type I CsLOBP | ATTCATATTAACGTTATCAATGATTTTTTTTAATAGTTTTACCACTTATTTTTTATAA | 60 |
| Type II CsLOBP | ATTCATATTAACGTTATCAATGATTTTTAAAAATAGTTTTACCACTTTTTTTTTATAA | 60 |
| Type I CsLOBP | CACCTTGGTAATTTTGACATTAGGTAGCAATATAATACGATAAAATTCACCTCCATGTAA | 120 |
| Type II CsLOBP | CACCTTGGTAATTTTGACATTAGGTAGCAATATAATACGATAAAATTCACCTCCATGTAA | 120 |
| Type I CsLOBP | TTTGAAGTTCTTTTCAATAATTTTTTGACAAATTTTATAGAAGAATTTAACCTTTT-TT | 179 |
| Type II CsLOBP | TTTGAAGTTCTTTTCAATAATTTTTTGACAAATTTTATAGAAGAATTTAACCTTTTCTT | 180 |
| Type I CsLOBP | TTTTTGGTTCAAACGAAGAAATGTTTCCGTCATTCAATTAAAATTAATGACATCATCTAG | 239 |
| Type II CsLOBP | TTTTTTTTCAAACGAAGAAATGTTTTCGTCATTCAATTAAAATTAATGACATCATCTAG | 240 |
| Type I CsLOBP | TGGCTGGTGACATACGCTTTAGATACAATTGTCATTCTTGCCTTTTCCTTTCTCTATAT | 299 |
| Type II CsLOBP | TGGCTGGTGACATACGCTTTAGATACGATTGTCATTCTTGCCTTTTCCTTTCTCTATAT | 300 |
| Type I CsLOBP | AAACCCGTTTTGCTTAACTTTGTTTCAACTAAAGCAGCTCCTCCTCATCCCTTACTGT | 359 |
| Type II CsLOBP | AAACCCGTTTTGCTTT-AACTTTGTTTCAACTAAAGCAGCTCCTCCTCATCCCTTACTGT | 359 |
| Type I CsLOBP | CTTTGCTTTCTCACTAACTACTACAACCAACAGTTTTCTTCTCTCAAAA | 409 |
| Type II CsLOBP | CTTCGCTTTCTCACTAACTACTACAACCAACAGTTTTCTTCTCTCAAAA | 409 |

Figure 7

| Off-targets | Representative chromatograms | Primers | Off-target Mutation |
|---|---|---|---|
| #1 | | P1: 5'-AGAACTTGACTTACGCACTCTTGTAA-3'<br>P2: 5'-AGTGCTGGTTCTAGTGAAACAGTT-3' | No |
| #2 | | P3: 5'-ACTGAGATCATCATCTCATGAT-3'<br>P4: 5'-TCTGTTGGAGACAAATCACCGGCA-3' | No |
| #3 | | P5: 5'-TGAGAATGTCATGTTGGGGATGA-3'<br>P6: 5'-ACAGCTTCAAGGTAGTCATTGCGT-3' | No |
| #4 | | P7: 5'-ATCCATCATTCACCACATGCTT-3'<br>P8: 5'-AGAAAATGGAAACAGCCATCAATA-3' | No |
| #5 | | P9: 5'-TGCCGGACATATTGTTACACCATAT-3'<br>P10: 5'-ACTACTAAGATGGATCATAGCCCT-3' | No |
| #6 | | P11: 5'-TGGTTAGAGAAATGTTACGCTCAA-3'<br>P12: 5'-TGTGAGGCATTTAGACACAGCCT-3' | No |
| #7 | | P13: 5'-TACCATATTGGAGGCACATGCTTT-3'<br>P14: 5'-TGGGCTCAACAATACGCCCAGTC-3' | No |
| #8 | | P15: 5'-ATTGGCCTAAGTCAGAACGGTAAA-3'<br>P16: 5'-TGAAAGATCAGTATGTTCTACCAT-3' | No |
| #9 | | P17: 5'-ACCACTTCAGGCAACTTCGCAAA-3'<br>P18: 5'-TGCTTGAGTTTGAGCACTTGGGGT-3' | No |

Figure 8

| | $D_{lab}2$ | $D_{lab}3$ | $D_{lab}9$ | $D_{lab}10$ | $D_{lab}11$ | $D_{lab}12$ |
|---|---|---|---|---|---|---|
| Total WT (Type I + Type II) | 68.42% | 76.20% | 10.64% | 11.21% | 53.09% | 48.88% |
| Total indel mutation rate | 31.58% | 23.80% | 89.36% | 88.79% | 46.91% | 51.12% |
| Total 1A insertion | 13.01% | 9.61% | 36.77% | 37.06% | 19.63% | 21.09% |
| Total 1T insertion | 7.36% | 4.97% | 19.76% | 21.99% | 12.12% | 10.66% |
| Total short deletion | 11.20% | 9.22% | 32.83% | 29.74% | 15.16% | 19.37% |

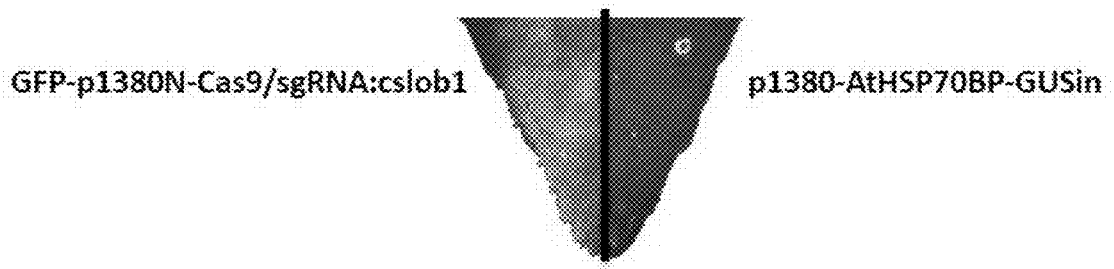
Figure 13A
Wild type (x85) AGGGCTAAGAACTATAGGCGGCGGAGA GAG GGGATCTGCAAGA
-GA (x5)      AGGGCTAAGAACTATAGGCGGCGGA - - GAG GGGATCTGCAAGA
+1A (x8)      AGGGCTAAGAACTATAGGCGGCGGAGAAGA GGGATCTGCAAGA
+1T (x2)      AGGGCTAAGAACTATAGGCGGCGGAGATGA GGGAGCTGCAAGA
           SNP
       PAM *
Figure 13B
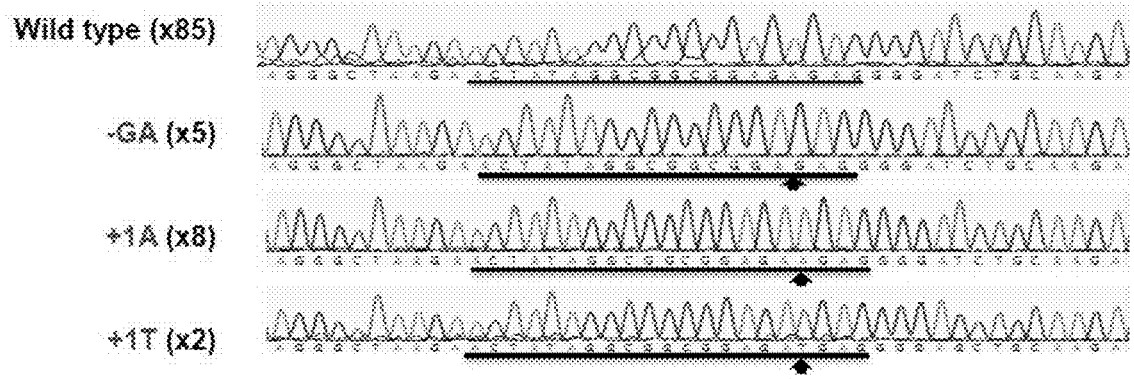
Figure 13C

| Off-targets | Representative chromatograms | Primers | Off-target Mutation |
|---|---|---|---|
| #1 (3X) (3X) (4X) | | P1: 5'-TGGGCATCCTAAAGTAAAGTAGAA-3'<br>P2: 5'-ACCTAGAGCTTCTACATTGAATCA-3' | No |
| #2 | | P3: 5'-AGTTGTTACCGTTACAGCGGTG-3'<br>P4: 5'-TGCTTGAAGATCTCTTCAATTCCC-3' | No |
| #3 | | P5: 5'-AGCGGCTACGAAATGGTACGTCTCGA-3'<br>P6: 5'-ACGAATAGCCTTGGGCCACTTCAC-3' | No |
| #4 | | P7: 5'-AGAAAGAGAAGATGATGGGAAAGAT-3'<br>P8: 5'-ACATGCCGAATAGAGGAAACGGTG-3' | No |
| #5 | | P9: 5'-AGCTAGCGCGTCGAATTGATTCTG-3'<br>P10: 5'-AGGCAGCTCTCTTCCTTATTGC-3' | No |
| #6 | | P11: 5'-AGTCAACAACGATACACCCAGCAG-3'<br>P12: 5'-TTCTCTGAGTATCAGCCCTATCAG-3' | No |
| #7 | | P13: 5'-TGTGCGTCAGGTCCAAGGAAGGTT-3'<br>P14: 5'-TGGAGCTTCCTAGCATAGGAGAAG-3' | No |

Figure 17

CITRUS VARIETIES RESISTANT TO *XANTHOMONAS CITRI* INFECTION

CROSS-REFERENCE TO RELATED APPLICATION

This application is a divisional of U.S. application Ser. No. 15/757,377 filed Mar. 5, 2018 which is a 371 of PCT International Application No. PCT/US2016/049878 filed Sep. 1, 2016 which claims the benefit of U.S. Provisional Application Ser. No. 62/214,623, filed Sep. 4, 2015, the disclosures of which are hereby incorporated by reference in their entirety, including all figures, tables and amino acid or nucleic acid sequences.

The Sequence Listing for this application is labeled "Seq-List.txt" which was created on Sep. 1, 2016 and is 25 KB. The entire content of the sequence listing is incorporated herein by reference in its entirety.

BACKGROUND OF THE INVENTION

Citrus is one of the most important crops and is grown worldwide. Global citrus production in 2013 exceeded 88 million metric tons, with an estimated value of S9 billion. New cultivars with desirable traits have been developed to improve citrus yield and nutritional value, as well as its capacity to adapt to biotic and abiotic stresses. However, conventional breeding is greatly challenged due to many limitations, e.g., narrow genetic diversity and long juvenile period. New technologies can improve citrus for disease resistance against citrus canker, citrus Huanglongbing and other diseases. Among them, citrus canker caused by *Xanthomonas citri* subsp. *citri* (Xcc) is one of the most devastating diseases and most commercial citrus varieties are susceptible to Xcc.

Presently, three technologies, including zinc finger nucleases (ZFNs), transcription activator-like effector nucleases (TALENs) and Cas9/sgRNA have been developed to modify genomes of different organisms. Cas9/sgRNA has been developed from type II clustered, regularly interspaced, short palindromic repeats (CRISPR)/CRISPR-associated protein Cas9. In *Streptococcus pyogenes* CRISPR system, Cas9 can be guided to specific genomic loci by a duplex consisting of mature CRISPR RNA (crRNA) and trans-activating crRNA, where the target DNA is cleaved. The CRISPR-associated Cas9 endonuclease contains the HNH and RuvC nuclease domains, which are responsible for cleavage of both strands of the target DNA.

CRISPR/Cas9 system has been simplified to a two-component system-Cas9/sgRNA, in which a synthetic single-guide RNA (sgRNA) can guide Cas9 to perform sequence-specific genome editing. Cas9/sgRNA system is attracting mounting attention since sgRNA composed of approximately 20 nucleotides is readily engineered, and multiple sgRNAs can be used to introduce mutations in several genes simultaneously, and well-designed sgRNA and Cas9 can lead to efficient mutations with minimal off-target effects. Cas9/sgRNA-mediated genome editing has been reported in bacterium, yeast, zebra fish, mice, rat, monkey, and plants. Till now, Cas9/sgRNA system has been successfully employed for genome modification in several plant species, including rice, wheat, tobacco, *Arabidopsis*, sorghum, tomato, maize, soybean and citrus.

In Valencia sweet orange (*Citrus sinensis*) and Duncan grapefruit (*C. paradisi* Macf.), Cas9/sgRNA system was employed to modify citrus CsPDS gene via Xcc-facilitated agroinfiltration, an optimized transient expression method in citrus. However, Cas9/sgRNA has not been harnessed for genome editing in transgenic citrus. Xcc, the causal agent of citrus canker, is a gram-negative bacterium that can infect most of citrus species, though some species are more susceptible than others. Via type III secretion system, a repertoire of Xcc-derived effectors, including transcription activator-like effector (TALE) PthA4, are injected into citrus host cells to suppress plant basal defenses, interfere with plant cellular processes to favor the pathogen growth and promote canker development. As a member of *Xanthomonas* AvrBs3 family-type III effectors (Boch and Bonas, 2010), PthA4 contains N-terminal translocation signal, 17.5 tandem repeat units of 34-amino-acids, three nuclear localizing signals and an acidic activation domain at its C-terminal end. Through its unique repeat units, PthA4 recognizes the corresponding promoter sequences in the host plant and activates the expression of citrus susceptibility genes that aid Xcc infection.

CsLOB1 is the disease susceptibility gene for citrus bacterial canker disease. Upon infection by Xcc, PthA4 is translocated from Xcc to host cells, where it induces CsLOB1 expression in a PthA4-dependent manner, leading to canker symptom development. PthA4 specifically binds to the effector binding elements ($EBE_{PthA4}$) in the CsLOB1 promoter region ($EBE_{PthA4}$-CsLOBP) to activate its gene expression. The sequence of the PthA4 effector binding elements is 5'-TATAAACCCCTTTTGCCTT-3' (SEQ ID NO: 1), and its complementary sequence is 5'-AAGGCAAAAGGGGTTTATA-3' (SEQ ID NO: 2).

BRIEF SUMMARY OF THE INVENTION

The invention provides that a mutation of the PthA4 effector binding elements in the promoter region of CsLOB1 can abolish the citrus canker development. Accordingly, an embodiment of the invention provides a binary vector, such as p1380N-Cas9/sgRNA:CsLOBP1, that disrupt the PthA4 EBEs in Type I CsLOB1 promoter (EBEPthA4-TI CsLOBP). The invention also provides transgenic citrus plants, for example, transgenic Duncan grapefruit plants, having one or more modifications to EBEPthA4-TI CsLOBP and that are resistant to Xcc infection.

The invention also provides that activation of a single allele of susceptibility gene CsLOB1 by PthA4 induces citrus canker disease and mutations of both alleles of the EBE region of the CsLOB1 gene, given that they could not be recognized by PthA4, are required to render certain citrus plants resistant to Xcc mediated citrus canker. As such, the invention provides a mutated citrus, for example, a mutated grapefruit plant, resistant to citrus canker, wherein the plant has a transgenic or non-transgenic biallelic mutation in which binding of Xcc PthA4 to the mutated promoters of CsLOB1 genes is reduced or absent.

Accordingly, the invention provides a plant cell or a plant having one or more mutations in the promoters of both the alleles for CsLOB1 gene, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of the CsLOB1 genes. The methods of making the plant cell or the plant resistant to infection by *Xanthomonas* spp. are also provided.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 7. Sequence alignment of Type I CsLOBP (SEQ ID NO: 109) and Type II CsLOBP (SEQ ID NO: 110) in Duncan grapefruit. $EBE_{PthA4}$-CsLOBP was indicated in blue. Artificial dTALE dCsLOB1.3 binding site was highlighted by green rectangle. The dCsLOB1.1 binding site was pointed out by blue rectangle and the dCsLOB1.2 binding site was highlighted by red rectangle.

FIG. 8. Potential off-targets of Cas9/sgRNA:CsLOBP1 in transgenic Duncan. Putative off-targets were analyzed (see HyperText Transfer Protocol://cbi.hzau.edu.cn/cgi-bin/CRISPR). Totally, 9 putative off-target sites were found and subjected for detailed sequencing analysis. P1 to P18 are SEQ ID NOs: 3 to 20, respectively.

FIGS. 10A-10B. Indel mutation rates and mutation genotypes in six CsLOB1 edited grapefruit lines. A. Mutation rate for each CsLOB1 edited grapefruit line. Targeted next generation sequencing was conducted for each line and more than 50,000 paired-end reads were generated for each sample. B. Representative indel mutation genotypes in Type I CsLOB1 plus Type II CsLOB1. The mutations included 1 bp insertion and short deletions. SEQ ID NO: 21 provides the sequence of the wild-type CsLOB1 Type I and SEQ ID NOs: 22-29 provide sequences of several Type I mutations. Similarly, SEQ ID NO: 30 provides the sequence of the wild-type CsLOB1 Type II and SEQ ID NOs: 31-38 provide sequences of several Type II mutations.

The AGAGAGGGGA(G/T)CTGCA (SEQ ID NO: 23 and 32) deletion and GGAGAGAGGGGA(G/T)CTGCAAGATTT (SEQ ID NO: 22 and 31) deletions removed the PAM and the SNP nucleotide. Star indicates SNP (single nucleotide polymorphism) used for differentiating type I and type II alleles of CsLOB1.

Figure 11:
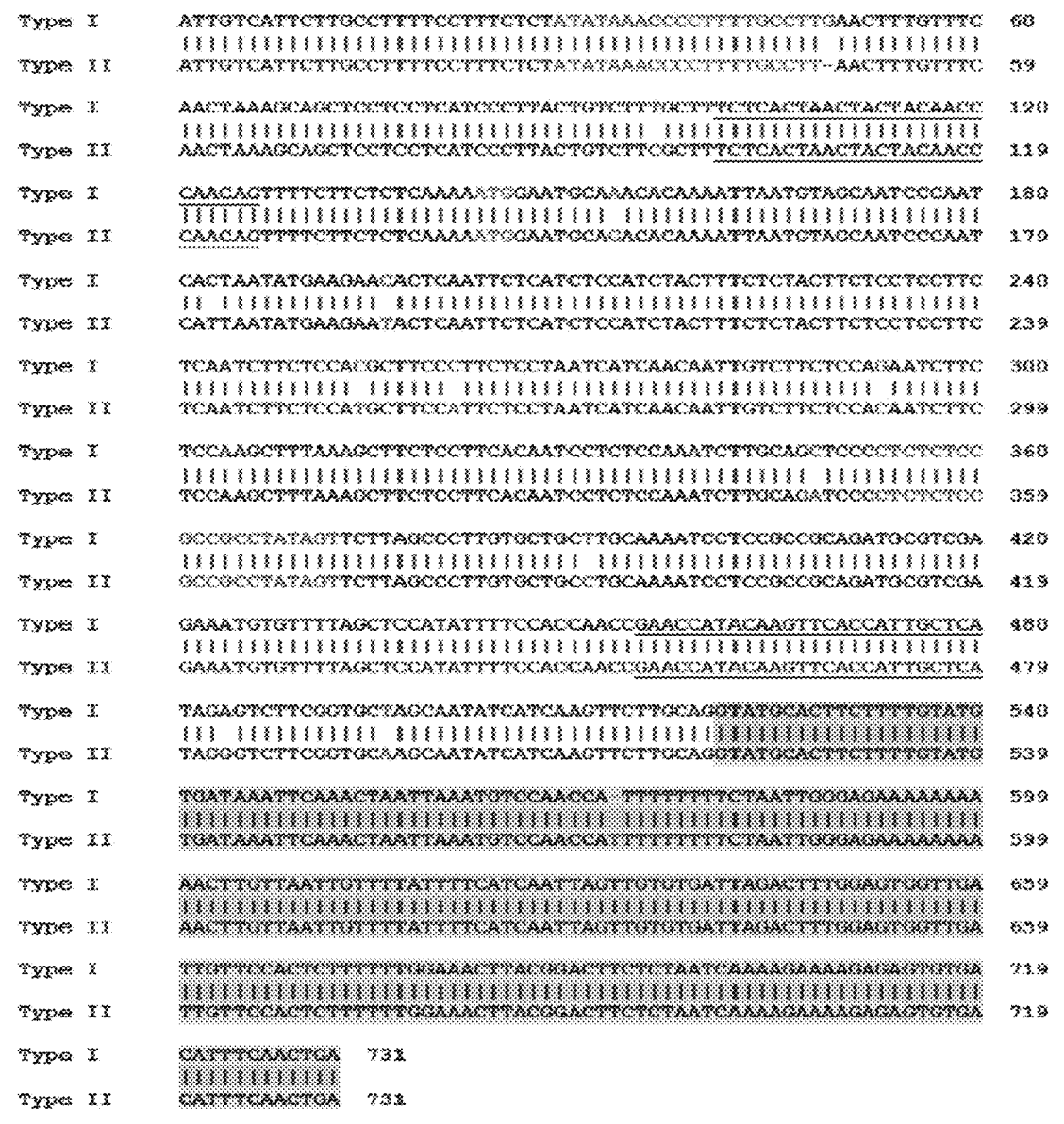

FIG. 11. Alignment of Type I CsLOB1 (SEQ ID NO: 39) and Type II CsLOB1 (SEQ ID NO: 40) in Duncan grapefruit. Two alleles of CsLOB1, Type I and Type II, are present in Duncan grapefruit. Part of the promoter regions and coding sequences are shown, in which the difference is indicated by purple, and the PthA4 effector binding elements are highlighted by blue. The intron is highlighted in grey. The translation start site is highlighted in green. The sgRNA-targeting region, which is conservative on both alleles, is highlighted in red. The primers are underlined, which are used to analyze indel mutation in genome modified Duncan by targeted next-generation sequencing.

Figure 12:
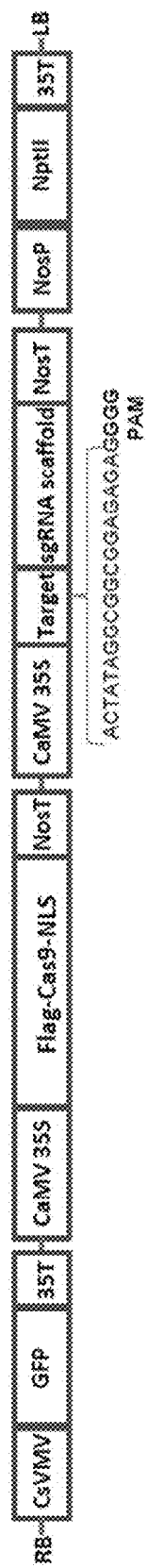
Figures 14A, 14B:
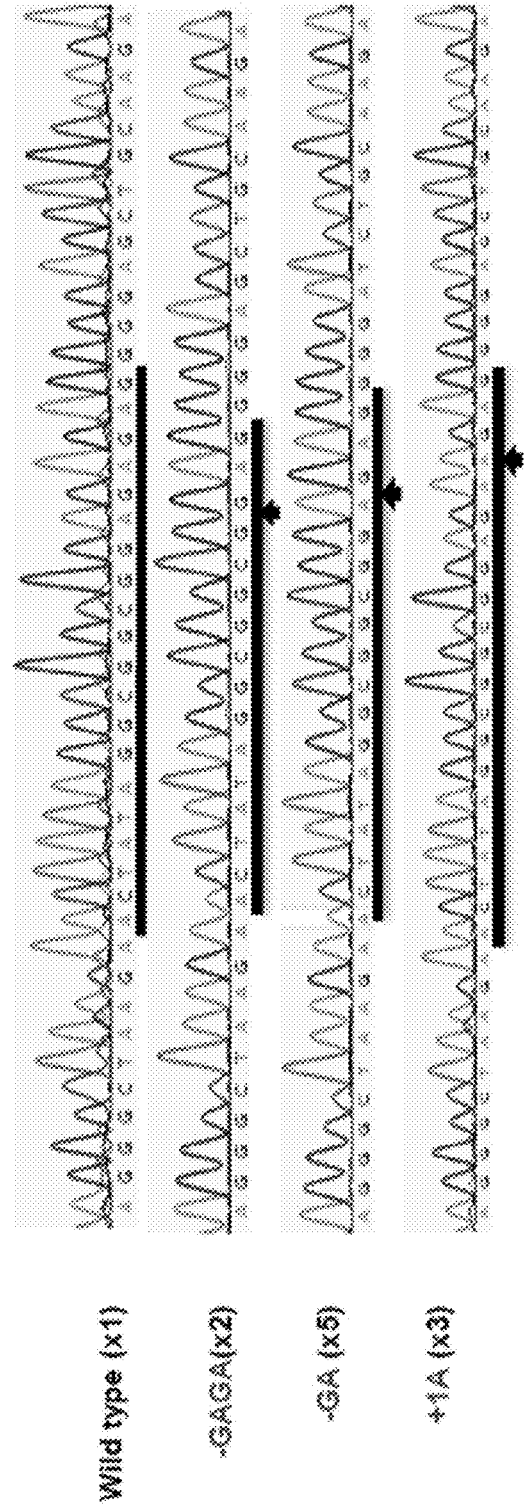
Figures 14C, 14D:
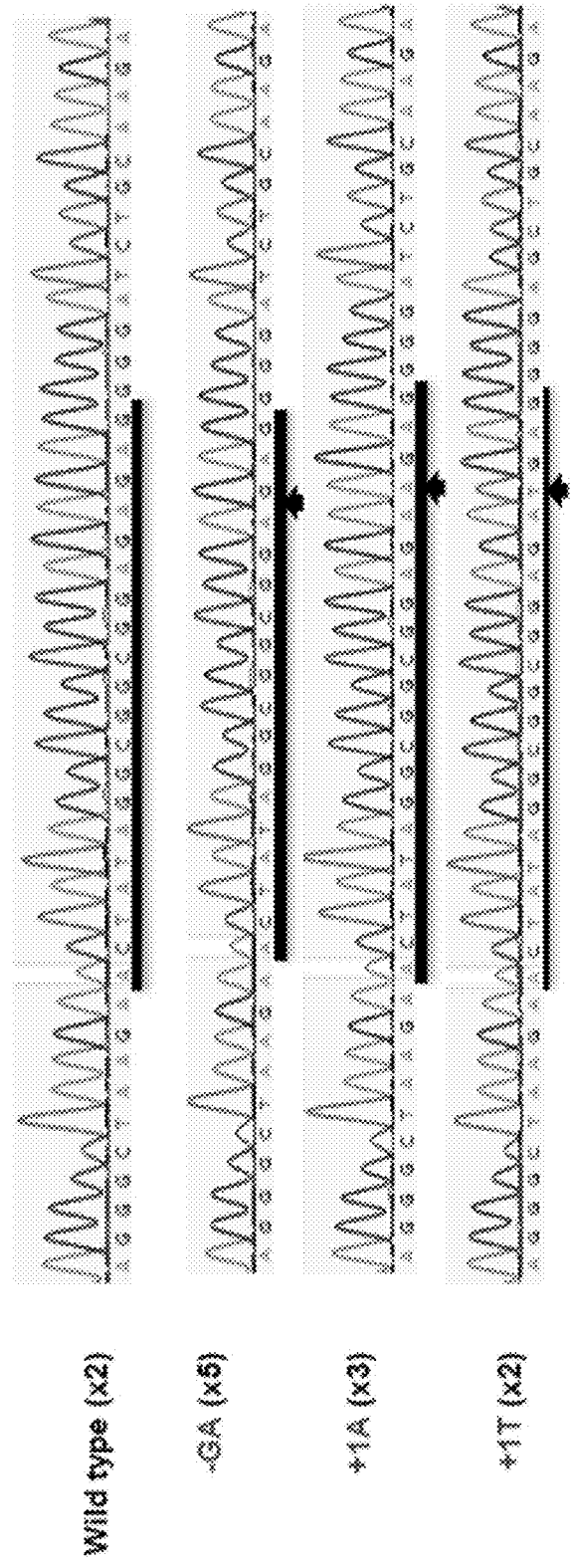

FIG. 12. Schematic of GFP-p1380N-Cas9/sgRNA:cslob1. CaMV 35S and 35T, the cauliflower mosaic virus 35S promoter and its terminator; NosP and NosT, the nopaline synthase gene promoter and its terminator; LB and RB, the left and right borders of the T-DNA region; Flag-Cas9-NLS, the Cas9 endonuclease containing Flag tag at its N-terminal and nuclear location signal at its C-terminal; target, the 20 nucleotides of CsLOB1 highlighted by red (first twenty nucleotides of SEQ ID NO: 41, indicated in red), was conserved on both alleles; sgRNA scaffold, a synthetic single-guide RNA composed of a fusion of CRISPR RNA and trans-activating CRISPR RNA; NptII, neomycin phosphotransferase II; GFP, green fluorescent protein; CsVMV, the cassava vein mosaic virus promoter; PAM, protospacer-adjacent motif.

FIGS. 13A-13C. Function analysis of GFP-p1380N-Cas9/sgRNA:cslob1 in Duncan leaves with the aid of GFP. (A) Four days after agroinfiltration with *Agrobacterium* cells harboring GFP-p1380N-Cas9/sgRNA:cslob1, GFP fluorescence was readily observed in Duncan grapefruit leaf. *Agrobacterium* cells harboring p1380-AtHSP70BP-GUSin were used as a negative control. (B) GFP-p1380N-Cas9/sgRNA:cslob1-directed modification to CsLOB1 coding region. The GFP-p1380N-Cas9/sgRNA:cslob1-targeted sequence in CsLOB1 was shown in red, and the mutations were shown in purple. The wild-type sequence is indicated as SEQ ID NO: 42 and the –GA, +1A, and +1T mutants are shown as SEQ ID NOs: 43, 44, and 45, respectively. (C) The representative chromatograms of CsLOB1 and its mutations. The targeted sequence within CsLOB1 is underlined by black lines, and the mutant site is indicated with an arrow. Single-nucleotide polymorphism (SNP) is indicated by an asterisk (*).

FIGS. 14A-14D. Representative chromatograms of CsLOB1 and its mutations in $D_{lob}9$ and $D_{lob}10$. Representative chromatograms of CsLOB1 and its mutations in $D_{lob}9$ transgenic plant (A, B) and #$D_{lob}10$ transgenic plant (C, D). The targeted sequence within CsLOB1 is shown by black lines, and the mutant site is pointed out by an arrow. In A, The wild-type sequence is indicated as SEQ ID NO: 42 and the –GAGA, –GA, and +1A mutants are shown as SEQ ID NOs: 46, 43, and 44, respectively. In C, the wild-type sequence is indicated as SEQ ID NO: 42 and the –GA, +1A, and +1T mutants are shown as SEQ ID NOs: 43, 44, and 45, respectively. Star indicates SNP.

Figure 15:
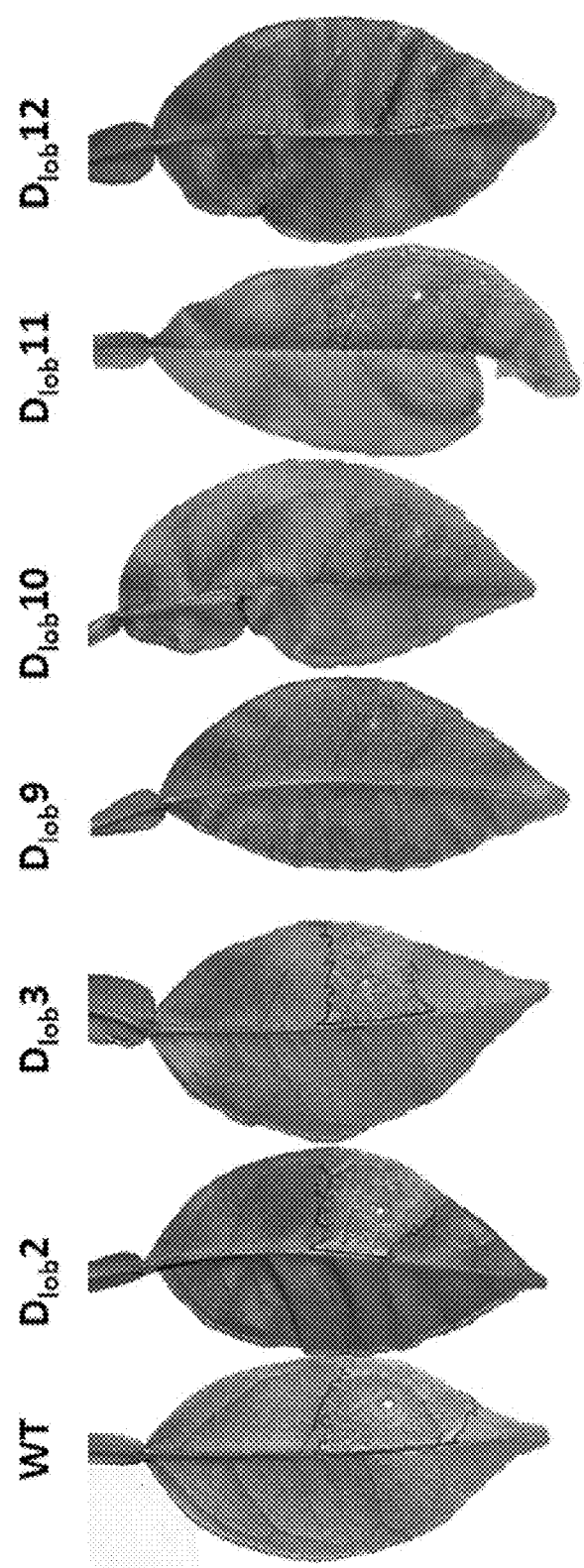

FIG. 15. The six CsLOB1 modified lines showed differential resistance to Xcc. At 5 days post inoculation with Xcc ($5\times10^8$ CFU/ml) using needleless *syringae*, canker symptoms were observed on normal grapefruit, $D_{lob}2$ and $D_{lob}3$. Canker symptoms were observed on DLOB9, DLOB10, DLOB11 and DLOB12 at 5 DPI even though at much reduced level compared to wild type grapefruit.

Figure 16:
Figure 16:

FIG. 16. No visible phenotypic changes for GFP-p1380N-Cas9/sgRNA:cslob1-transformed Duncan grapefruit lines. The GFP-p1380N-Cas9/sgRNA:cslob1-transformed plants were grown in glasshouse.

FIG. 17. Potential off-targets of GFP-p1380N-Cas9/sgRNA:cslob1 in transgenic Duncan. Putative off-targets were analyzed (see HyperText Transfer Protocol://cbi.hzau.edu.cn/cgi-bin/CRISPR). Totally, 7 putative off-target sites were found and subjected to detailed sequencing analysis. P1 to P14 are SEQ ID NOs: 47 to 60, respectively.

DETAILED DISCLOSURE OF THE INVENTION

Citrus canker caused by Xcc is a severe disease for most commercial citrus cultivars and is responsible for significant economic losses worldwide. Generating canker resistant citrus varieties provide an efficient and sustainable solution to control citrus canker. The invention provides canker resistant grapefruit by modifying the effector binding elements (EBEs) of PthA4 in the CsLOB1 Promoter ($EBE_{PthA4}$-CsLOBP) of the CsLOB1 gene or by inactivation of the CsLOB1 gene. CsLOB1 is a susceptibility gene for citrus canker and is induced by the pathogenicity factor PthA4, which binds to the $EBE_{PthA4}$-CsLOBP to induce CsLOB1 gene expression.

CsLOB1 in Duncan grapefruit has two alleles, Type I and Type II. An embodiment of the invention provides a binary vector, such as p1380N-Cas9/sgRNA:CsLOBP1, to disrupt the PthA4 EBEs in Type I CsLOB1 Promoter (TI CsLOBP) via epicotyl transformation of Duncan grapefruit. Four transgenic Duncan plants were created. Targeted modification to EBEPthA4-TI CsLOBP was verified. Type II CsLOB1 promoter was not mutated. Sequencing the PCR products amplified from transgenic plants indicated that Cas9/sgRNA-mediated modifications occurred mostly in somatic cells. As for Type I CsLOB1 promoter, the mutation rate was 15.63% (#D13), 14.29% (#D17), 54.54% (#D18), and 81.25% (#D22). In the presence of wild type Xcc, transgenic Duncan grapefruit developed canker symptoms similarly to wild type Duncan grapefruit. An artificially designed dTALE dCsLOB1.3, which specifically recognizes Type I CsLOBP, but not mutated Type I CsLOBP and Type II CsLOBP, was developed to infect Duncan transformants. Consequently, #D18 had weakened canker symptoms and #D22 had no visible canker symptoms in the presence of XccΔpthA4:dCsLOB1.3. Therefore, activation of a single allele of susceptibility gene CsLOB1 by PthA4 is sufficient to induce citrus canker disease and mutation of the promoters of both alleles of CsLOB1 is required to generate citrus canker resistant plants.

Accordingly, an embodiment of the invention provides a plant cell having one or more mutations in the promoters of both the alleles for CsLOB1 gene, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of CsLOB1 genes. Based on the invention described herein, a person of ordinary skill in the art can determine the binding site for PthA4 protein from *Xanthomonas* spp. in the promoters of CsLOB1 genes as well as appropriate mutations which reduce or abolish the binding of the *Xanthomonas* spp. PthA4 protein on to the binding sites in the promoters of CsLOB1 genes.

For the purpose of this invention a gene typically includes a promoter and a protein coding region and further optionally comprises a 5' untranslated region and/or a 3' untranslated region. The protein coding region can comprise one or more exons and introns. The introns, 5' untranslated region and/or the 3' untranslated region may be absent in a gene.

As used herein, the term "plant" includes reference to whole plants, plant organs (e.g., leaves, stems, roots, etc.), seeds, plant cells, and progeny of same. Parts of plants are to be understood within the scope of the invention comprise, for example, plant cells, protoplasts, tissues, callus, embryos as well as flowers, stems, fruits, ovules, leaves, or roots originating in plants or their progeny. As used herein, the term "plant cell" includes, without limitation, seeds suspension cultures, embryos, meristematic regions, callus tissue, leaves, roots, shoots, gametophytes, sporophytes, pollen, and microspores. Monocotyledonous and dicotyledonous plants can be transformed with a promoter or DNA construct as disclosed herein.

The plant cell can be homozygous or heterozygous for CsLOB1 gene. In one embodiment, the plant cell is homozygous for CsLOB1 gene. In another embodiment, the plant cell is heterozygous for CsLOB1 gene and the two alleles of CsLOB1 gene comprise CsLOB1 Type I and CsLOB1 Type II.

The plant cell can be from a monocot or a dicot plant. In certain embodiments, the plant cell is from a citrus plant cell. Non-limiting examples of a citrus include grapefruit, orange, lime, lemon, mandarin, papeda and pummelo. Additional examples of citrus plants are well known to a person of ordinary skill in the art and such embodiments are within the purview of the invention.

The cells having one or more mutations in the promoters of both the alleles for CsLOB1 gene can be grown in to plants according to methods known in the art. See, for example, McCormick et al. (1986) Plant Cell Reports 5:81-84. These plants may then be grown, and either pollinated with the same modified plant variety or different varieties, to produce hybrid having a desired phenotypic characteristic. Two or more generations may be grown to ensure that the resistant to infection by *Xanthomonas* spp. is stably maintained and inherited and then seeds harvested to ensure that the resistant to infection by *Xanthomonas* spp. has been achieved. Thus as used herein, "seeds" refers to seeds that contain the one or more mutations in the promoters of both the alleles for CsLOB1 gene.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif.). This regeneration and growth process typically includes the steps of selection of plant cells of interest, culturing those cells through the usual stages of embryonic development through the rooted plantlet stage. Embryos and seeds are similarly regenerated. The resulting rooted shoots are thereafter planted in an appropriate plant growth medium such as soil. The regenerated plants are generally self-pollinated to provide modified plants.

Accordingly, a further embodiment of the invention provides a plant having one or more mutations in the promoters of both the alleles for CsLOB1 genes, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of the CsLOB1 genes.

The plant can be homozygous or heterozygous for CsLOB1 gene. In one embodiment, the plant is homozygous for CsLOB1 gene. In another embodiment, the plant is heterozygous for CsLOB1 gene and the two alleles of CsLOB1 gene comprise CsLOB1 Type I and CsLOB1 Type II.

The plant can be a monocot or a dicot plant. In certain embodiments, the plant is a citrus plant. Non-limiting examples of a citrus include grapefruit, orange, lime, lemon, mandarin, papeda and pummelo. Additional examples of citrus plants are well known to a person of ordinary skill in the art and such embodiments are within the purview of the invention.

A further embodiment provides a seed of the plant, wherein the seed comprises the one or more mutations in the promoters of both the alleles for CsLOB1 genes, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of the CsLOB1 genes. The seed of the invention, when grown in to a plant, produces a plant having one or more mutations in the promoters of both the alleles for CsLOB1 genes, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of the CsLOB1 genes.

An even further embodiment provides a method introducing one or more mutations in the promoters of both the alleles for CsLOB1 genes of a plant or a plant cell, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of the CsLOB1 genes. Methods of introducing one or mutations according to the invention are well known to a person of ordinary skill in the art and such embodiments are within the purview of the invention.

A further embodiment of the invention provides a binary vector, such as p1380N-Cas9/sgRNA:CsLOBP1 or GFP-p1380N-Cas9/sgRNA:cslob1, that is designed to disrupt the coding sequence in the CsLOB1 gene, for example, via transformation of Duncan grapefruit. Inactivation/disruption of the CsLOB1 gene coding region confers resistance to infection by *Xanthomonas* spp. In plants or plant cells in which the gene has been inactivated or disrupted.

Accordingly, an embodiment of the invention provides a plant cell having one or more mutations in the coding regions of both the alleles for CsLOB1 gene, wherein the one or more mutations reduce or abolish the function of CsLOB1 protein. Based on the invention described herein, a person of ordinary skill in the art can determine appropriate mutations which reduce or abolish the function of CsLOB1 protein.

In one aspect, the mutation in the coding region of CsLOB1 gene is accomplished without introducing any exogenous genetic material. Another aspect provides for the mutation of endogenous genes by the introduction of one or more point mutation(s) or by introducing one or more stop codon(s) in the open reading frame of CsLOB1 gene. In another aspect, the open reading frame of CsLOB1 gene or a portion thereof is deleted from the chromosomal DNA of a plant cell. In certain aspects, an exogenous nucleotide sequence may be introduced to inactivate CsLOB1 gene. Additional examples of mutations in the coding region of CsLOB1 gene that can inactivate the CsLOB1 protein are known to a person of ordinary skill in the art and such embodiments are within the purview of the invention.

The cells having one or more mutations in the coding region of both the alleles for CsLOB1 gene can be grown in to plants according to methods known in the art. See, for example, McCormick et al. These plants may then be grown, and either pollinated with the same modified plant variety or different varieties, to produce hybrid having a desired phenotypic characteristic. Two or more generations may be grown to ensure that the resistant to infection by *Xanthomonas* spp. is stably maintained and inherited and then seeds harvested to ensure that the resistant to infection by *Xanthomonas* spp. has been achieved. Thus as used herein, "seeds" refers to seeds that contain the one or more mutations in the coding regions of both the alleles for CsLOB1 gene.

Accordingly, a further embodiment of the invention provides a plant having one or more mutations in the coding region of both the alleles for CsLOB1 genes, wherein the one or more mutations reduce or abolish the function of CsLOB1 protein.

The plant can be homozygous or heterozygous for CsLOB1 gene. In one embodiment, the plant is homozygous for CsLOB1 gene. In another embodiment, the plant is heterozygous for CsLOB1 gene and the two alleles of CsLOB1 gene comprise CsLOB1 Type I and CsLOB1 Type II. In a further embodiment, a different mutation causes reduction or abolishment of the function of CsLOB1 protein.

The plant can be a monocot or a dicot plant. In certain embodiments, the plant is a citrus plant. Non-limiting examples of a citrus include grapefruit, orange, lime, lemon, mandarin, papeda and pummelo. Additional examples of citrus plants are well known to a person of ordinary skill in the art and such embodiments are within the purview of the invention.

A further embodiment provides a seed of the plant, wherein the seed comprises the one or more mutations in the coding region of both the alleles for CsLOB1 genes, wherein the one or more mutations reduce or abolish the function of CsLOB1 protein. The seed of the invention, when grown in to a plant, produces a plant having one or more mutations in the coding regions of both the alleles for CsLOB1 genes, wherein the one or more mutations reduce or abolish the function of CsLOB1 protein.

An even further embodiment provides a method of introducing one or more mutations in the coding region of both the alleles for CsLOB1 genes of a plant or a plant cell, wherein the one or more mutations reduce or abolish the function of CsLOB1 protein.

Materials and Methods

Plasmid Construction

Figure 1A:
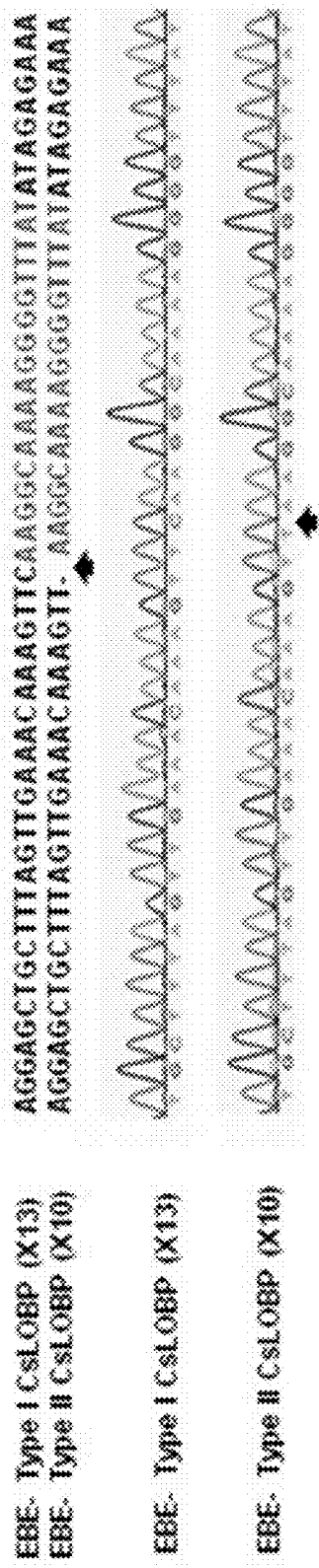
FIGS. 1a-1c. CsLOBP of Duncan grapefruit and binary vectors. (a) Two kinds of CsLOBP, Type I (SEQ ID NO: 95) and Type II (SEQ ID NO: 96), in Duncan grapefruit, and part of their sequences and chromatograms are shown, in which the difference (1 bp) was indicated by arrows, and the PthA4 effector binding elements were highlighted by blue. Among 23 colonies sequenced, 13 belong to Type I CsLOBP, and 10 belong to Type II CsLOBP. (b) A sgRNA (sgRNA: CsLOBP1) was designed to target $EBE_{pthA4}$-TI CsLOBP (SEQ ID NO: 97), with the target indicated by blue; sgRNA: CsLOBP1 (SEQ ID NO: 98), with the targeting site was underlined by a red line. (c) Schematic diagram of p1380N-Cas9/sgRNA:CsLOBP1 CaMV 35S and 35T, the cauliflower mosaic virus 35S promoter and its terminator; NosP and NosT, the nopaline synthase gene promoter and its terminator; LB and RB, the left and right borders of the T-DNA region; Flag-Cas9-NLS, the Cas9 endonuclease containing Flag tag at its N-terminal and nuclear location signal at its C-terminal; target, the 20 nucleotides of $EBE_{pthA4}$-TI CsLOBP highlighted by red, was located upstream of protospacer-adjacent motif (PAM) (SEQ ID NO: 99); sgRNA scaffold, a synthetic single-guide RNA composed of a fusion of CRISPR RNA and trans-activating CRISPR RNA; NptII, the coding sequence of neomycin phosphotransferase II.

The CaMV 35S promoter was amplified using primers CaMV35-5-XhoI (5'-A CTCGAGACTAGTACCATGGTGGACTCCTCTTAA-3', SEQ ID NO: 61) and sgRNA-CsLOBP1-1 (5'-phosphorylated-AACTTTGTTTCCCTCTCCAAATGAAAT-GAACTTC-3', SEQ ID NO: 62), and the sgRNA-NosT fragment was amplified using primers sgRNA-CsLOBP1-2 (5'-phosphorylated-CAAGGCAAAGTTT-TAGAGCTAGAAATAGCAA-3', SEQ ID NO: 63) and NosT-3-AscI (5'-ACCTGGGCCC GGCGCGCCGATCTAGTAACATAGATGA-3', SEQ ID NO: 64). Through three-way ligation, XhoI-digested CaMV35S and AscI-cut sgRNA-NosT were inserted into XhoI-AscI-treated p1380N-Cas9 to form p1380N-Cas9/sgRNA:CsLOBP1 (FIG. 1c). The p1380N-Cas9 was described previously (Jia et al. (2014b).

Figure 3A:
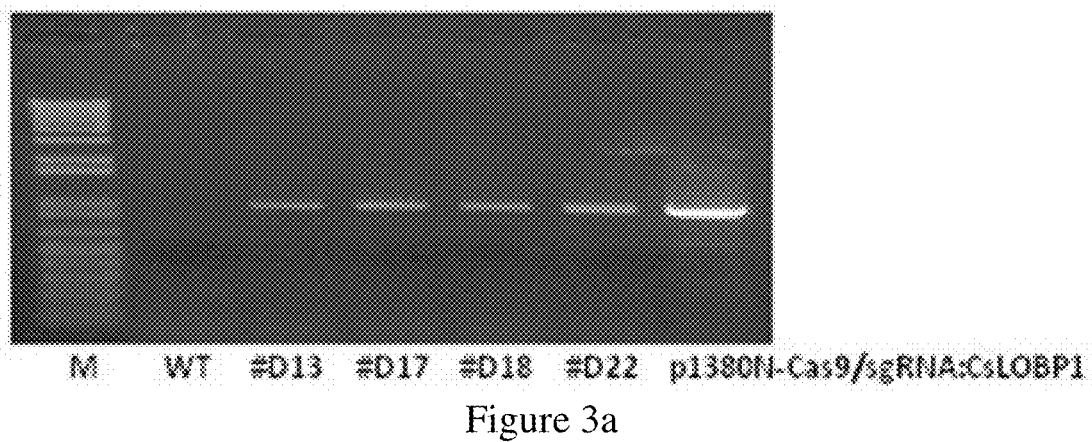
FIGS. 3a-3d. Cas9/sgRNA:CsLOBP1-directed $EBE_{PthA4}$-TI CsLOBP modification in transgenic Duncan grapefruit. (a) Four Cas9-sgRNA:CsLOBP1-transformed Duncan grapefruit plants (#D13, #D17, #D18, and #D22) were established, which were PCR-positive using primers Npt-5 and 35T-3. Plasmid p1380N-Cas9/sgRNA:CsLOBP1 was used as a positive control. M, 1 kb DNA ladder; WT, wild type. (b) Cas9/sgRNA:CsLOBP1-induced mutations in grapefruit $EBE_{PthA4}$-TI CsLOBP. The Type I CsLOBP (SEQ ID NO: 95) sequence targeted by Cas9/sgRNA:CsLOBP1 was shown in red, and the mutations were shown in purple. Among 124 colonies sequenced, there were 58 Type I CsLOBP, 33 Type II CsLOBP (SEQ ID NO: 96), and 33 mutant Type I CsLOBP (SEQ ID NO: 101 and 102). (c) The representative chromatograms of Type I CsLOBP and its mutations (SEQ ID NO: 101 and 102). The targeted sequence within the Type I CsLOBP was indicted by black lines, and the mutant sites were highlighted by arrows. (d) The representative chromatograms of PCR product direct sequencing. The PCR products were amplified from wild type Duncan (SEQ ID NO: 103) and four transgenic plants (SEQ ID NOs: 104-104), and primer CsLOB4 was used for direct sequencing. The beginning sites of double peak/multiple peaks were highlighted by arrows.
Figures 3B, 3C:
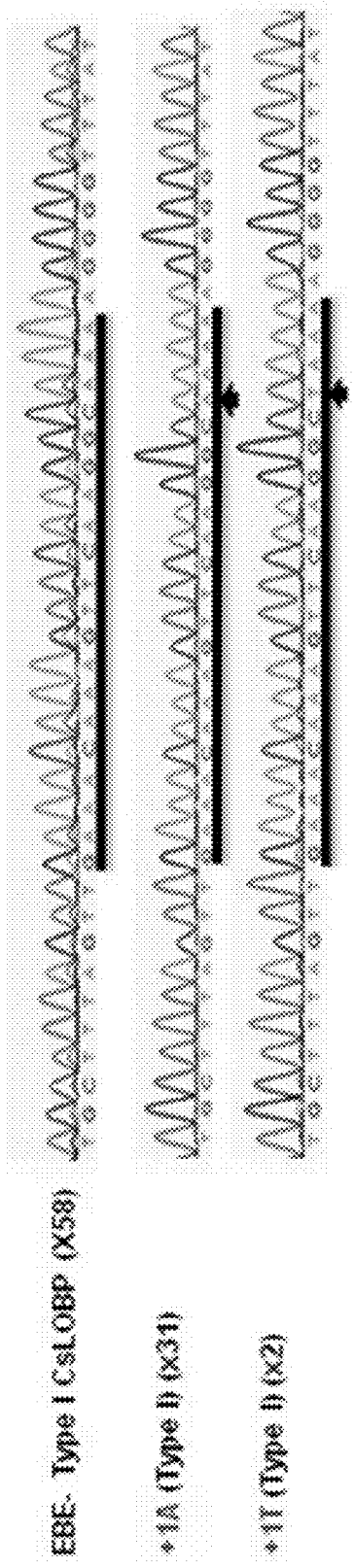
Figure 4A:
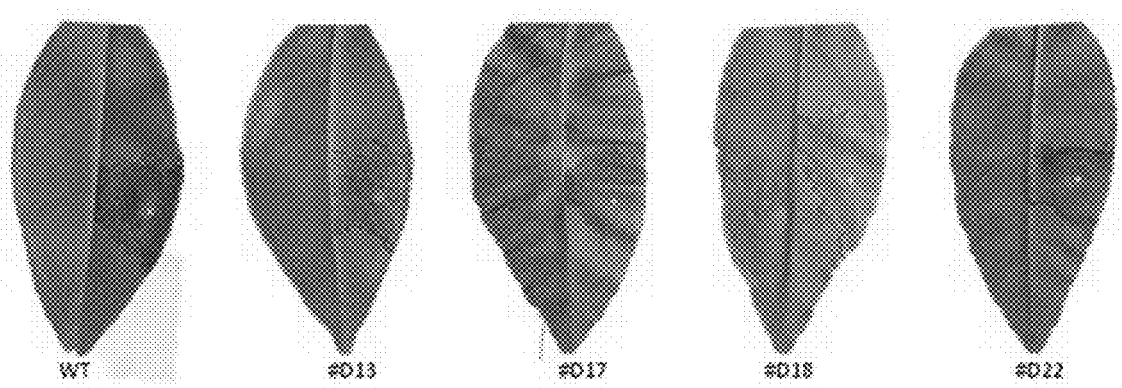
FIGS. 4a-4d. Pathogenicity assay for Cas9/sgRNA:CsLOBP1-transformed Duncan grapefruit and GUS assay for CsLOBP. (a) Five days post inoculation, similar canker symptoms were readily detected on wild type and transgenic Duncan grapefruit. (b) Schematic diagram of three binary plasmids (p1380-TI CsLOBP-GUSin, p1380-TII CsLOBP-GUSin and p1380-MTI CsLOBP-GUSin) developed in this work. TI CsLOBP, Type I CsLOBP of Duncan grapefruit; TII CsLOBP, Type II CsLOBP; MTI CsLOBP, mutant Type I CsLOBP; GUSin, the intron-containing β-glucuronidase; HptII, the coding sequence of hygromycin phosphotransferase II. (c) Via Xcc-facilitated agroinfiltration, quantitative GUS assay and GUS histochemical staining were used to evaluate the effects of Xcc-derived PthA4 on CsLOBPs. The results indicated that PthA4 could activate GUS expression under the control of Type I CsLOBP, Type II CsLOBP or mutant Type I CsLOBP, but not affect GUS expression directed by AtHSP70B. SD values were calculated from three replicates of one experiment. The experiments were repeated twice with similar results. (d) Quantitative RT-PCR analyses of CsLOB1 expression in Duncan plants. The expression levels of CsLOB1 were analyzed at 48 hours post-inoculation of Xcc (right bar graphs) or water (left bar graphs) on Duncan grapefruit. The expression was normalized to housekeeping gene CsEF1α. Data bars represent the mean±SD with three technical replicates of one experiment.
Figure 4B:
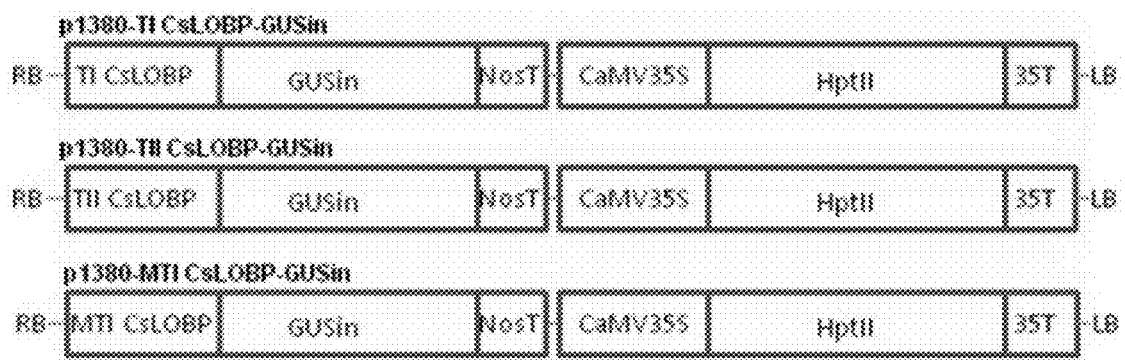

Using forward primer LOBP1 (5'-AGGT AAGCTTTCTCTATATAAACCCCTTT-3', SEQ ID NO: 65) and reverse primer LOBP2 (5'-ACCT GGATCCTTTTGAGAGAAGAAAACTGTTGGGT-3', SEQ ID NO: 66), the Type I CsLOBP and Type II CsLOBP were PCR-amplified from wild-type Duncan grapefruit, and mutant Type I CsLOBP, which contained an adenine insertion (FIG. 3b), was amplified from transgenic Duncan grapefruit #D22. After sequencing, the PCR products were digested with HindIII and BamHI, and inserted into HindIII-BamHI-treated p1380-35S-GUSin to form binary vectors p1380-TI CsLOBP-GUSin, p1380-TII CsLOBP-GUSin and p1380-MTI CsLOBP-GUSin (FIG. 4b). Binary vector p1380-AtHSP70BP-GUSin was developed previously (Jia and Wang, 2014b). The binary vectors were introduced into *A. tumefaciens* strain EHA105 by the freeze-thaw method. Recombinant *Agrobacterium* cells were cultivated for Xcc-facilitated agroinfiltration or epicotyl citrus transformation.

The EcoRI-PthA4-HindIII fragment from p53-pthA4 was cloned into EcoRI-HindIII-digested pBluecript SK⁺ to form pSK-pthA4. StuI-Goldengate-AatII fragment from pTAL2 (Addgene plasmid #31033) was insert into pSK-pthA4, which was treated with StuI and AatII, to produce pSKpthA4-Ta12. The RVDs of artificial dCsLOB1.3 were developed using the Golden Gate method, and linked to pSK-pthA4-Ta12 to construct pSK-dCsLOB1.3. The EcoRI-dCsLOB1.3-HindIII fragment derived from pSK-dCsLOB1.3 was ligated with HindIII-EcoRI-digested p53-pthA4 to yield the complementary plasmid p53-dCsLOB1.3, which was introduced into XccΔpthA4 to form XccΔpthA4:dCsLOB1.3.

The CaMV 35S promoter was amplified using primers CaMV35-5-XhoI (5'-A CTCGAGACTAGTACCATGGTGGACTCCTCTTAA-3', SEQ ID NO: 61) and sgRNA-cslob1-P1 (5'-phosphorylated-TATAGTCCTCTCCAAATGAAATGAACTTC-3', SEQ ID NO: 67), and the sgRNA-NosT fragment was amplified using primers sgRNA-cslob1-P2 (5'-phosphorylated-GGCGGCGGAGAGAGGTTT-TAGAGCTAGAAATAGCAA-3', SEQ ID NO: 68) and NosT-3-AscI (5'-ACCTGGGCCC GGCGCGCCGATCTAGTAACATAGATGA-3', SEQ ID NO: 64). Through three-way ligation, XhoI-digested CaMV35S and AscI-cut sgRNA-NosT were inserted into XhoI-AscI-treated p1380N-Cas9 to form p1380N-Cas9/sgRNA:cslob1. The p1380N-Cas9 was described previously (Jia et al. (2014b).

Using a pair of primers 35T-P1 (5'-AGGT GGATCCGAGCTCGAAAATTTCTCCA TAATAATGTGTGAGT-3', SEQ ID NO: 69) and 35T-P2 (5'-AGGTATTAATAAGCTTCG GGGGATCTGGATTT-TAGTACT-3', SEQ ID NO: 70), the CaMV 35S terminator was amplified, and cloned into BamHI-AseI-digested p1380N-Cas9 to produce p1380-35S-35T. The cassava vein mosaic virus promoter (CsVMV) was amplified using primers CsVMV-5-SpeI (5'-AGGT ACTAGTAAGCTTGCATGCCCGCGCCAGAAGGTAAT-TATCCAAG-3', SEQ ID NO: 71) and CsVMV-3-SalI (5'-AGGTGTCGACAAACTTACAAATTTCTCTG AAG-3', SEQ ID NO: 72) from plasmid AtSUC2-NPR1, and the GFP fragment was amplified using primers GFP-5-XhoI (5'-AGGTCTCGAGATGAAGACTAATCTTTTTCTCT-3', SEQ ID NO: 73) and GFP2 (5'-TC GAGCTCTTAAAGCTCATCATGTTTGTAT-3', SEQ ID NO: 74) from p1380-35S-GFP. Through three-way ligation, SpeI-CsVMV-SalI fragment and XhoI-GFP-SacI were inserted into SpeI-SacI-treated p1380-35S-35T to form p1380-CsVMV-GFP-35T. After digestion with HindIII, the HindIII-CsVMV-GFP-35T-HindIII fragment from p1380-CsVMV-GFP-35T was cloned into p1380N-Cas9/sgRNA:cslob1 to obtain GFP-p1380N-Cas9/sgRNA:cslob1.

The binary vector GFP-p1380N-Cas9/sgRNA:cslob1 was introduced into *A. tumefaciens* strain EHA105 competent cells by the freeze-thaw method. Recombinant *Agrobacterium* cells were employed for citrus transformation or Xcc-facilitated agroinfiltration (described below).

Duncan CsLOB1 Sequencing and Analysis

Figures 9A, 9B:
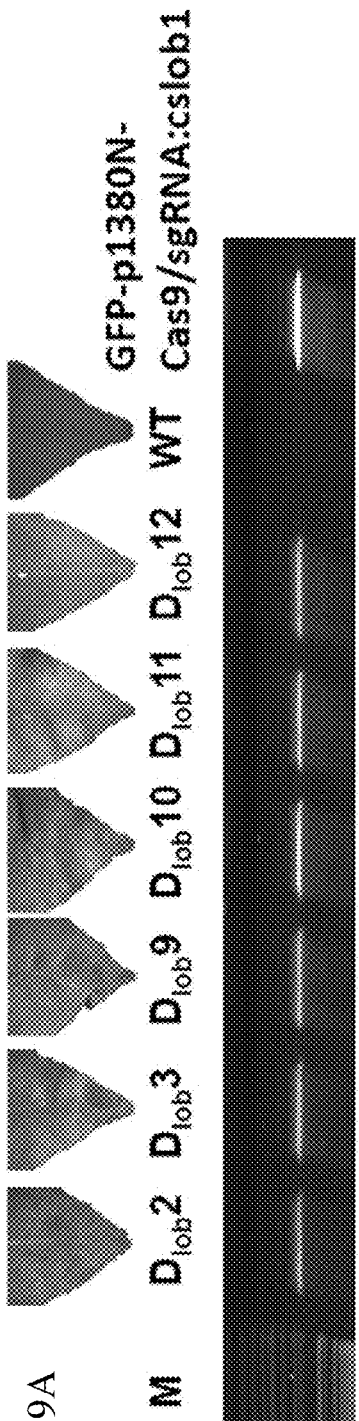
FIGS. 9A-9C. Analysis of GFP-p1380N-Cas9/sgRNA:cslob1-transformed Duncan grapefruit. A. Six GFP-p1380N-Cas9/sgRNA:cslob1-transformed Duncan grapefruit plants ($D_{lob}2$, $D_{lob}3$, $D_{lob}9$, $D_{lob}10$, $D_{lob}11$, and $D_{lob}12$) were GFP positive. The wild type grapefruit plant did not show GFP. B. The six transgenic lines contain Cas9/sgRNA as indicated by PCR amplification using primers 355P-5-P1 and NosP-3-P2. Plasmid GFP-p1380N-Cas9/sgRNA:cslob1 was used as a positive control. M, 1 kb DNA ladder; WT, wild type. C. The six CsLOB1 modified lines showed differential resistance to Xcc. At 4 days post inoculation with Xcc ($5\times10^8$ CFU/ml) using a needleless syringe, canker symptoms were observed on normal grapefruit, $D_{lob}2$ and $D_{lob}3$, but absent or reduced on $D_{lob}9$, $D_{lob}10$, $D_{lob}11$, and $D_{lob}12$.

Using a Wizard Genomic DNA Purification Kit (Promega), genomic DNA was extracted from wild type Duncan, or transgenic plants, or the GFP-positive Duncan leaves treated by *Xanthomonas citri* ssp. *citri* (Xcc)-facilitated agroinfiltration of GFP-p1380N-Cas9/sgRNA:cslob1 (FIG. 9A). To analyze CsLOB1 gene in detail, PCR was performed with the Phusion DNA polymerase (New England Biolabs) and a pair of primers, CsLBDP-5-P1 (5'-ATTGTCAT-TCTTGCCTTTTCCTTTCT-3', SEQ ID NO: 75) and CsLOB1-3-P2 (5'-TCAGTTGAAATGTCACACTCTCTT-3', SEQ ID NO: 76), flanking part of CsLOB1 promoter and its coding region. By blunt end cloning, the PCR products were inserted into the PCR-BluntII-TOPO vector (Life Technologies). The colonies were randomly selected for DNA sequencing and the results were visualized by Chromas Lite program.

For PCR product direct sequencing, CsLBDP-5-P1 and CsLOB1-3-P2 were used to amplify the DNA fragments from genomic DNA. The PCR products were purified and subjected to direct sequencing using primer CsLOB1-P2 (5'-TGAGCAATGGTGAACTTGTATGGTTC-3', SEQ ID NO: 77). The results were analyzed by Chromas Lite program.

Xcc-Facilitated Agroinfiltration in Duncan Grapefruit

Duncan grapefruit plants, grown in a greenhouse at temperatures ranging from 25 to 30° C., were pruned to produce uniform shoots before Xcc-facilitated agroinfiltration. Xcc-facilitated agroinfiltration in citrus leaves was carried out as described by Jia et al. (2014a) and Jia et al. (2014b), with minor modification. Briefly, citrus leaves were inoculated with a culture of actively growing Xcc re-suspended in sterile tap water ($5 \times 10^8$ CFU/ml). One day later, *Agrobacterium* cells harboring p1380N-Cas9/sgRNA:CsLOBP1, p1380-TI CsLOBP-GUSin, p1380-TII CsLOBP-GUSin, p1380-MTI CsLOBP-GUSin or p1380-AtHSP70BP-GUSin, were used for agroinfiltration in the same area. In the case of XccΔpthA4:dCsLOB1.3-facilitated agroinfiltration, the XccΔpthA4:dCsLOB1.3-treated leaf areas were subjected to agroinfiltration with recombinant *Agrobacterium* containing p1380-TI CsLOBP-GUSin, p1380-TII CsLOBP-GUSin, p1380-MTI CsLOBP-GUSin or p1380-AtHSP70BP-GUSin. Four days after agroinfiltration, leaves were collected for genomic DNA extraction or GUS assay.

Whenever applicable, Duncan leaves were inoculated with a culture of actively growing XccΔgumC re-suspended in sterile tap water ($5 \times 10^8$ CFU/ml). Twenty-four hours later, the XccΔgumC-treated leaf areas were agroinfiltrated with recombinant *Agrobacterium* cells harboring GFP-p1380N-Cas9/sgRNA:cslob1 or p1380-AtHSP70BP-GUSin (Jia et al., 2014b). Four days after agroinfiltration, leaves were subjected to GFP observation or genomic DNA extraction.

GFP Detection

Four days after Xcc-facilitated agroinfiltration with GFP-p1380N-Cas9/sgRNA:cslob1 or p1380-AtHSP70BP-GUSin, GFP fluorescence in the treated leaves was visualized under illumination of an EBQ 100 isolated light source using a Zeiss Stemi SV11 dissecting microscope equipped with an Omax camera. The leaf was photographed using the Omax Toupview software.

*Agrobacterium*-Mediated Duncan Grapefruit Transformation

Citrus transformation was performed as reported in Orbović et al. (2015). 2250 Duncan epicotyl segments and 3682 Valencia segments were used as explants for transformation by recombinant *Agrobacterium* cells harboring binary vector p1380N-Cas9/sgRNA:CsLOBP1. The transgenic plants were subjected to PCR analysis with a pair of primers, Npt-5 (ATTGAACAAGATGGATTGCACG, SEQ ID NO: 78) and 35T-3 (TTCGGGGGATCTGGATTT-TAGTAC, SEQ ID NO: 79).

Similarly, about 2923 Duncan epicotyl explants were co-incubated with recombinant *Agrobacterium* cells harboring binary vector GFP-p1380N-Cas9/sgRNA:cslob1. Five weeks later, about 839 shoots sprouted from these explants after co-incubation. All explants were inspected for the presence of GFP fluorescence. In the initial screen, 15 shoots were designated as positive and micro-grafted on 'Carrizo' citrange rootstock plants [*Citrus sinensis* (L.) Osbeck x *Poncirus trifoliata* (L.) Raf.]. Out of these shoots, 7 died upon grafting in in vitro conditions before they were transferred to pots. Additional 2 plants were discarded based on unsatisfactory level of GFP fluorescence detected in their tissue during secondary inspection. The six remaining GFP-positive plants were used for further analysis.

DNA from CsLOB1 modified grapefruit lines was used as template, and the primers listed in Table 1 were used to amplify the fragment containing the off-targets. Finally, the PCR products were ligated with PCR-BluntII-TOPO vector for sequencing analysis.

TABLE 1

Analysis of indel mutations for Type I CsLOB1 and Type II CsLOB1 in six transgenic Duncan grapefruit lines

|  | #DLOB2 | #DLOB3 | #DLOB9 | #DLOB10 | #DLOB11 | #DLOB12 |
|---|---|---|---|---|---|---|
| Type I-Wild Type | 28.20% | 45.45% | 3.08% | 3.77% | 23.35% | 16.00% |
| Type I-(-GGAGAGAGGGGAGCTGCAAGATTT) | 0.82% | 0.26% | 1.75% | 1.86% | 0.44% | 1.11% |
| Type I-(-AGAGAGGGGAGCTGCA) | 0.37% | 0.25% | 0.60% | 0.46% | 0.33% | 0.60% |
| Type I-(-GGAGAGAGG) | 0.47% | 0.14% | 0.65% | 0.51% | 0.28% | 0.44% |
| Type I-(-GGCGGAG) | 0.37% | 0.40% | 0.77% | 0.62% | 0.47% | 0.47% |
| Type I-(-GAGA) | 0.47% | 0.39% | 1.32% | 1.11% | 0.59% | 0.98% |
| Type I-(-GA) | 3.20% | 2.95% | 8.75% | 7.69% | 4.85% | 6.34% |
| Type I-(+1A) | 7.96% | 5.64% | 18.52% | 18.72% | 11.05% | 12.31% |
| Type I-(+1T) | 4.85% | 3.20% | 10.44% | 12.10% | 7.05% | 6.08% |
| Type II-Wild Type | 40.22% | 30.75% | 7.56% | 7.44% | 29.74% | 32.88% |
| Type II-(-GGAGAGAGGGGATCTGCAAGATTT) | 0.79% | 0.30% | 1.71% | 1.83% | 0.69% | 1.07% |
| Type II-(-AGAGAGGGGATCTGCA) | 0.23% | 0.14% | 0.62% | 0.70% | 0.21% | 0.42% |
| Type II-(-GGAGAGAGG) | 0.02% | 0.06% | 0.09% | 0.10% | 0.00% | 0.00% |
| Type II-(-GGCGGAG) | 0.44% | 0.70% | 1.28% | 1.15% | 0.58% | 0.51% |
| Type II-(-GAGA) | 0.49% | 0.45% | 1.92% | 1.93% | 0.69% | 1.16% |
| Type II-(-GA) | 3.53% | 3.19% | 13.37% | 11.78% | 6.01% | 6.27% |
| Type II-(+1A) | 5.05% | 3.97% | 18.25% | 18.34% | 8.58% | 8.78% |
| Type II-(+1T) | 2.51% | 1.77% | 9.32% | 9.89% | 5.08% | 4.58% |
| Total Type I insertion (1A + 1T) | 12.81% | 8.84% | 28.96% | 30.82% | 18.10% | 18.39% |
| Total Type II insertion (1A + 1T) | 7.56% | 5.74% | 27.57% | 28.23% | 13.65% | 13.36% |
| Total Type I short deletion | 5.70% | 4.38% | 13.83% | 12.26% | 6.96% | 9.94% |
| Total Type II short deletion | 5.51% | 4.84% | 18.99% | 17.48% | 8.20% | 9.43% |

The GFP-p1380N-Cas9/sgRNA:cslob1-transformed plants were subjected to PCR analysis with a pair of primers, 35SP-5-P1 (5'-ATCAAAGGCCATGGAGTCAAA-3', SEQ ID NO: 80) and NosP-3-P2 (5'-TTGTCGTTTCCCGCCTTCAGT-3', SEQ ID NO: 81).

Next Generation Sequencing Analysis

Genomic DNA from six transgenic plants was used as templated for PCR amplification using a pair of primers, CsLOB1-P1 (5'-TCTCACTAACTACTACAACC-CAACAG-3', SEQ ID NO: 82) and CsLOB1-P2 (FIG. 11). All PCR products were pooled to construct the DNA library for sequencing using an Illumina HiSeq 2500 platform at Novogene (Beijing, China). For each sample, more than 50,000 paired end reads were generated. After de-multiplex, barcode and primer deletion using custom Perl script, the raw reads were quality trimmed using sickle software with parameters average quality 30 and reads length threshold 200 bp (Fass et al.). The remaining high quality reads were clustered with a threshold of 100% pairwise identity using UCLUST (Edgar et al.). The representative sequences from abundant clusters with relative abundance >1% were aligned using MEGA 6 (Tamura et al.) and further analyzed for mutation genotype.

Xcc Infection Assay

Wild type Duncan grapefruit and CsLOB1 modified grapefruit lines were grown in a glasshouse. The same age leaves were inoculated with Xcc ($5 \times 10^8$ CFU/ml) using a needleless syringe. After inoculation, citrus canker formation was observed and photographed at different time points.

Analysis of Potential Off-Targets

To analyze potential off-targets of GFP-p1380N-Cas9/sgRNA:cslob1 in CsLOB1 modified grapefruit lines, the putative off-targets were analyzed using a web-based software (http://cbi.hzau.edu.cn/cgi-bin/CRISPR). Genomic Duncan CsLOBP Sequencing and Analysis Using a Wizard Genomic DNA Purification Kit (Promega), genomic DNA was extracted from wild type Duncan grapefruit, or transgenic Duncan plants (#D13, #D17, #D18, #D22), or the Duncan leaves treated by Xcc-facilitated agroinfiltration with p1380N-Cas9/sgRNA:CsLOBP1-transformed *Agrobacterium* (FIG. 1c). Using 200 ng of genomic DNA as template, PCR was used to amplify Duncan grapefruit CsLOBP with the Phusion DNA polymerase (New England Biolabs) and a pair of primers, LOBP3 (5'-AGGTAAGCTTATTCATATTAACGTTA TCAATGATT-3', SEQ ID NO: 83) and LOBP2. By blunt end cloning, the PCR products were ligated into the PCR-BluntII-TOPO vector (Life Technologies) for DNA sequencing, and Chromas Lite program was employed to analyze the sequencing results. For PCR product direct sequencing, the CsLOBP3-CsLOBP2-amplified PCR products were purified and subjected to sequencing using primer CsLOB4 (5'-CGTCATTCAATTAAAATTAATGAC-3', SEQ ID NO: 84). The results were analyzed by Chromas Lite program.

GUS Assay

Four days after Xcc-facilitated agroinfiltration, the histochemical staining of GUS and the quantitative GUS assay were performed for the treated Duncan grapefruit leaves as described in Jia et al. (2014b).

Extraction of Total RNA from Duncan Plants and Quantitative RT-PCR Analysis

Duncan grapefruit leaves were syringe-infiltrated with Xcc suspensions at $5 \times 10^8$ CFU/ml or tap water. Forty-eight hours later, total RNA was extracted from Duncan plants using the RNeasy Plant Mini Kit (Qiagen), according to the manufacturer's instructions. All quantitative RT-PCRs were performed using an Applied Biosystems 7500 Fast Real-time PCR system (Foster City, Calif., USA) with a QuantiTect SYBR Green RT-PCR kit (Qiagen). The primers, CsLOB5 (5'-TCCACCAACCGAACCATACA-3', SEQ ID NO: 85) and CsLOB6 (5'-GGCACTTGCTTCATAGAC-CAT-3', SEQ ID NO: 86), were designed to amplify CsLOB1, and CsEF1α-P1 (5'-GTAACCAAGTCTGCTGC-CAAG-3', SEQ ID NO: 87) and CsEF1α-P2 (5'-GACC-CAAACACCCAACACATT-3', SEQ ID NO: 88) were employed to amplify Citrus sinencis elongation factor 1 α (CsEF1α), which was used as endogenous control. The total reaction volume of one-step qRT-PCR was 20 µl and contained 2×QuantiTect SYBR Green RT-PCR Master Mix (10 µl), 10 µm gene-specific primers (1 µl), QuantiTect RT Mix (0.4 µl) and 50 ng of RNA template (1 µl). Reactions were incubated at 50° C. for 30 min, and at 95° C. for 15 min, cycled (40 times) at 94° C. for 15 s, 54° C. for 30 s and 72° C. for 30s. The relative fold change in target gene expression was calculated using the formula 2' of Livak et al. (2001). The experiment was repeated twice with similar results.

Canker Symptom Assay in Citrus

Duncan grapefruit (*Citrus paradisi*), pummelo (Citrus maxima), Valencia sweet orange (*Citrus sinensis*) and transgenic Duncan grapefruit were grown in a greenhouse. Before Xcc inoculation, the plants were pruned. The same age leaves were treated with Xcc or XccΔpthA4: dCsLOB1.3, which was re-suspended in sterile tap water (5×10⁸ CFU/ml). At different time points, citrus canker development was observed and photographed.

Analysis of Potential Off-Target Sequences

Cas9/sgRNA analysis software, (see, hypertext transfer protocol: cbi.hzau.edu.cn/cgi-bin/CRISPR), was used to identify potential off-target sequences of Cas9/sgRNA: CsLOBP1-targeting site, which is GAAACAAAGTT-CAAGGCAAA (SEQ ID NO: 89). Using genomic DNA from #D13, #D17, #D18 and #D22, these potential off-targets were amplified by PCR using the primers shown in FIG. 8. By blunt end cloning, the PCR products were inserted into PCR-BluntII-TOPO vector for sequencing analysis.

FIG. 8 provides potential off-targets of Cas9/sgRNA: CsLOBP1 in transgenic Duncan. The 9 potential off-targets were numbered #1, #2, #3, #4, #5, #6, #7, #8 and #9, respectively.

The potential off-target sequences were highlighted by purple rectangle.

Potential GFP-p1380N-Cas9/sgRNA:cslob1-directed off-target mutagenesis in Duncan grapefruit was also analyzed. The putative off-targets were identified as described by Lei et al. Seven putative off-targets were identified (FIG. 17) Amplification and Sanger sequencing were used to identify the putative off-target mutations. No off-target mutation was identified in the six CsLOB1 modified plants (FIG. 17). However, since only ten random colonies per putative off-target site were subjected to sequencing analysis, the possibility of off-target mutagenesis could not be ruled out.

Seven potential off-targets were numbered as #1, #2, #3, #4, #5, #6 and #7. The potential off-target sequences were highlighted by a purple rectangle. Three kinds of SNPs exist for #1 potential off-target and one kind of SNP exists for #7. Arrow indicates SNP.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Two Types of Cslob1 Promoters in Duncan Grapefruit

The Valencia CsLOBP was shown to be different from that of Duncan grapefruit. Grapefruit resulted from hybridization between pummelo (*C. maxima*) and sweet orange (*C. sinensis*). To identify whether Duncan grapefruit contains CsLOBP from both pummelo and sweet orange, CsLOBP was amplified from Duncan grapefruit and sequenced after blunt end cloning. Among 23 random colonies, thirteen contained the Valencia-type CsLOBP, which is designated as Type I CsLOBP, and ten were the same as pummelo CsLOBP, named as Type II CsLOBP (FIGS. 1*a* and 7). This is consistent with the report that two types of CsPDS gene are present in Duncan grapefruit. The two types of CsLOBPs are different in several regions (FIG. 7), and notably, one nucleotide C next to $EBE_{PthA4}$ is missing in the Type II CsLOBP (FIG. 1*a*).

Figure 1B:
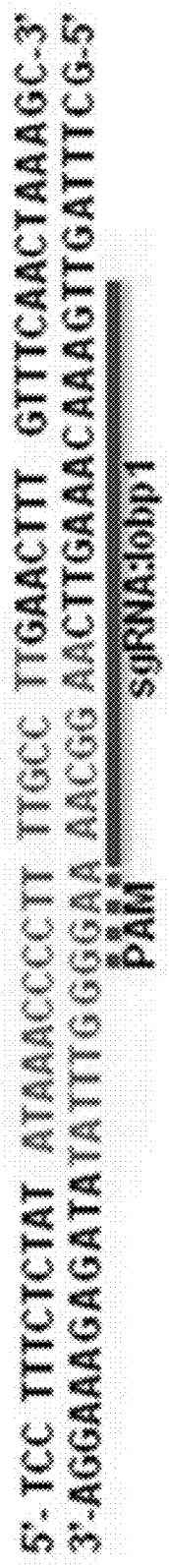
Figure 1C:
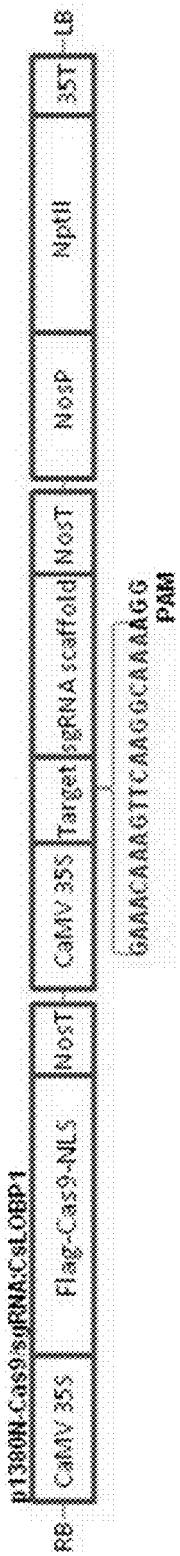
Figure 2A:
FIGS. 2a-2b. Cas9/sgRNA:CsLOBP1-mediated $EBE_{PthA4}$-TI CsLOBP modification via Xcc-facilitated agroinfiltration in Duncan grapefruit leaves. (a) Targeted mutations induced by Cas9/sgRNA:CsLOBP1 to grapefruit $EBE_{pthA4}$-TI CsLOBP. The p1380N-Cas9/sgRNA:CsLOBP1-targeted sequence in Type I CsLOBP (SEQ ID NO: 95) was shown in red, and the mutations were shown in purple. Among 100 colonies sequenced, there were 55 Type I CsLOBP, 43 Type II CsLOBP, and 2 mutant Type I CsLOBP. The results verified that only Type I CsLOBP could be targeted by Cas9/sgRNA:CsLOBP1 (SEQ ID NO: 100). (b) The representative chromatograms of Type I CsLOBP and its mutations (SEQ ID NO: 100). The targeted sequence within Type I CsLOBP was shown by black lines, and the mutant site was pointed out by an arrow.
Figure 2B:
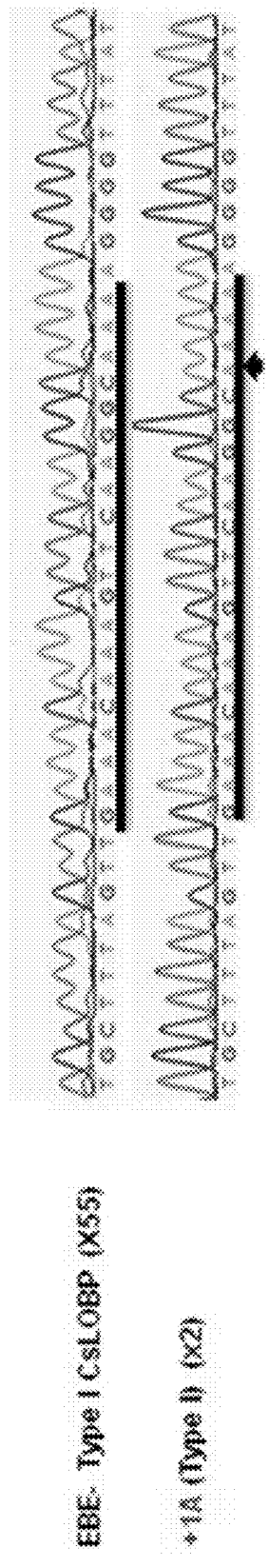

Example 2—Designing Cas9/SGRNA:CsLOBP1 to Modify $EBE_{PthA4}$-Type I (TI) CsLOBP in Duncan Grapefruit Via Xcc-Facilitated Agroinfiltration Based on Type I CsLOBP sequence, the binary vector, p1380N-Cas9/sgRNA:CsLOBP1, was developed to target $EBE_{PthA4}$-TI CsLOBP (FIGS. 1*b* and 1*c*). Xcc-facilitated agroinfiltration was firstly employed to test whether Cas9/sgRNA:CsLOBP1 was functional. Xcc-facilitated agroinfiltration is fast compared to the time-consuming transgenic approach. 100 colonies were randomly selected for sequencing. Two among 57 Type I CsLOBP sequences contained the Cas9/sgRNA:CsLOBP1-directed modifications, whereas no modification was observed among 43 Type II CsLOBP sequences (FIG. 2). Therefore, Cas9/sgRNA:CsLOBP1 is functional for Type I CsLOBP targeting.

Example 3—Use of Cas9/SGRNA:CsLOBP1 to Modify $EBE_{PthA4}$-Type I CsLOBP in Transgenic Duncan Grapefruit Duncan grapefruit and Valencia sweet orange was subjected to *Agrobacterium*-mediated epicotyl transformation. Four independent transgenic lines, #D13, #D17, #D18 and #D22, were successfully created from Duncan grapefruit, and verified by PCR analysis (FIG. 3*a*). On the other hand, no transgenic Valencia was obtained. Based on sequencing results, targeted modifications to $EBE_{PthA4}$-Type I CsLOBP were observed (FIGS. 3*b* and 3*c*, and Table 2) in transgenic Duncan plants, i.e., five indels of $EBE_{PthA4}$-TI CsLOBPs among 32 sequences in #D13, three mutations among 21 sequences in #D17, 12 mutations among 22 sequences in #D18, and 13 mutations among 16 sequences in #D22 (Table 2). All Cas9/sgRNA:CsLOBP1-induced mutations were 1 bp insertion (FIGS. 3*b* and 3*c*), occurred at the 4th base from the PAM site, which could be attributable to the fact that Cas9 nuclease cleaves its target at a position 3 bp upstream of the PAM sequence. Consistently, Cas9/sgRNA-directed mutations in transgenic *Arabidopsis* were predominantly 1 bp insertion and short deletions, and more than half of the mutations resulting from Cas9/sgRNA activities were 1 bp insertion in transgenic rice. $EBE_{PthA4}$-Type II CsLOBP was not modified which confirmed the results obtained from Xcc-facilitated agroinfiltration (FIG. 2). For Type I CsLOBP, the Cas9/sgRNA:CsLOBP1-mediated mutation rate was 15.63% (#D13), 14.29% (#D17), 54.54% (#D18) and 81.25% (#D22) (Table 2). Therefore, Cas9/sgRNA can be harnessed to modify citrus genome in transgenic plants. Intriguingly, only a proportion of $EBE_{PthA4}$-Type I CsLOBP was edited by Cas9/sgRNA:CsLOBP1 in four transgenic lines, which is consistent with the results obtained from Cas9/sgRNA-transformed Arabidopsis.

Figure 3D:
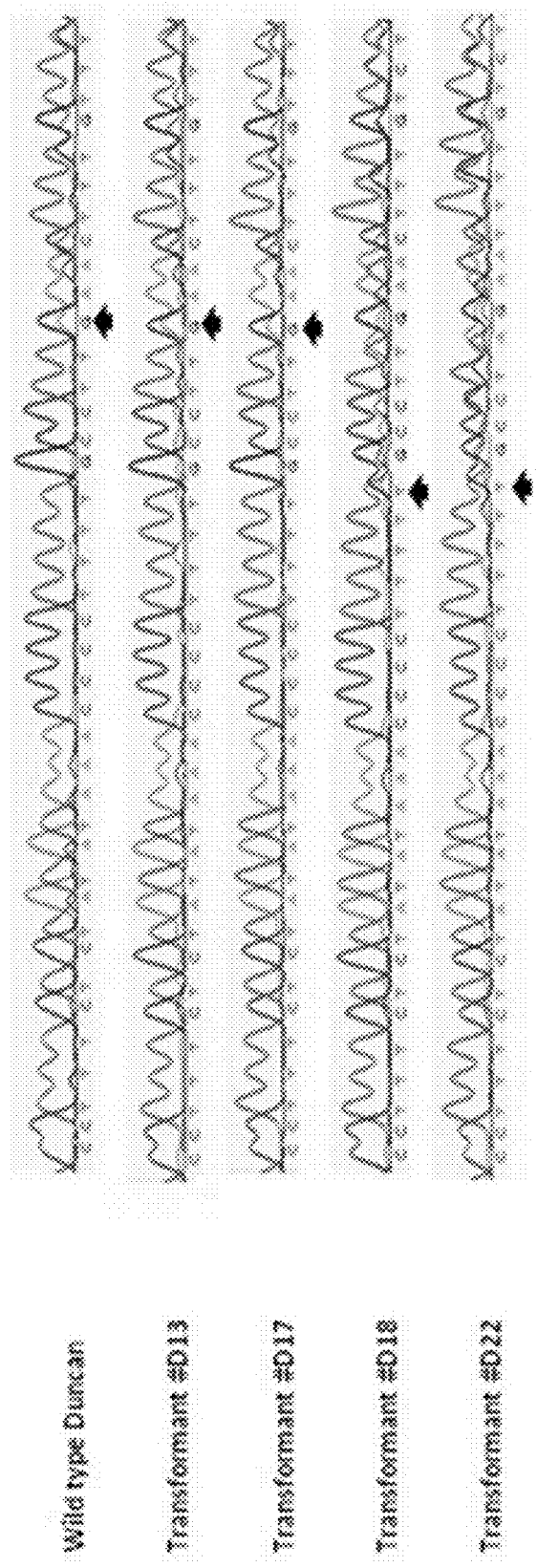

Cas9/sgRNA-mediated modifications in T1 Arabidopsis plants occurred mostly in somatic cells during development. PCR products from transgenic Duncan were sequenced to determine whether Cas9/sgRNA:CsLOBP1-directed mutations occurred in citrus somatic cells, as did in transgenic Arabidopsis. Multiple peaks were observed at the targeted site in #D18 and #D22 from the $5^{th}$ thymine (FIG. 3d), whereas double peak was present from the unique guanine in wild type Duncan, #D13 and #D17 (FIG. 3d). Notably, the chromatogram of #D13 and #D17 was similar to that of wild type Duncan, and different from that of #D18 and #D22 (FIG. 3d). Mutation efficiencies of #D13 and #D17 were likely to be so low that the Cas9/sgRNA:CsLOBP1-mediated mutated Type I CsLOBP could not be detected by PCR sequencing. Since Cas9/sgRNA:CsLOBP1 was designed to modify $EBE_{PthA4}$-Type I CsLOBP in Duncan grapefruit (FIGS. 1b and 1c), it is unlikely to create bi-allelic mutation in the first generation. In Cas9/sgRNA-transformed Arabidopsis, no bi-allelic modification in the first generation was observed, probably, since the gene modifications detected in T1 plants mostly occurred in somatic cells, whereas bi-allelic events were reported in transgenic tomato, since a pair of sgRNAs were employed to target slago7. A pair of $EBE_{PthA4}$-targeting sgRNAs can be used to introduce bi-allelic mutation for $EBE_{PthA4}$-CsLOBP in Valencia sweet orange, which contains only Type I CsLOBP.

TABLE 2

Molecular and genetic analysis of Cas9/sgRNA:CsLOBP1-induced mutations in 4 transgenic Duncan grapefruit.

| EBE-CsLOBP | Plant | | | | |
|---|---|---|---|---|---|
| | WT | #D13 | #D17 | #D18 | #D22 |
| WT Type I | 13 | 27 | 18 | 10 | 3 |
| Mutant Type I | 0 | 5 | 3 | 12 | 13 |
| Total Type I | 13 | 32 | 21 | 22 | 16 |
| WT Type II | 10 | 7 | 9 | 5 | 12 |
| Mutant Type II | 0 | 0 | 0 | 0 | 0 |
| Total Type II | 10 | 7 | 9 | 5 | 12 |
| Total Type I + II | 23 | 39 | 30 | 27 | 28 |
| Type I mutation rate (Mutant Type I/ Total Type I) | 0% | 15.63% | 14.29% | 54.54% | 81.25% |

Example 4—all Cas9/SGRNA:CsLOBP1-Transformed Plants were Susceiptible to Xcc

Figure 4C:
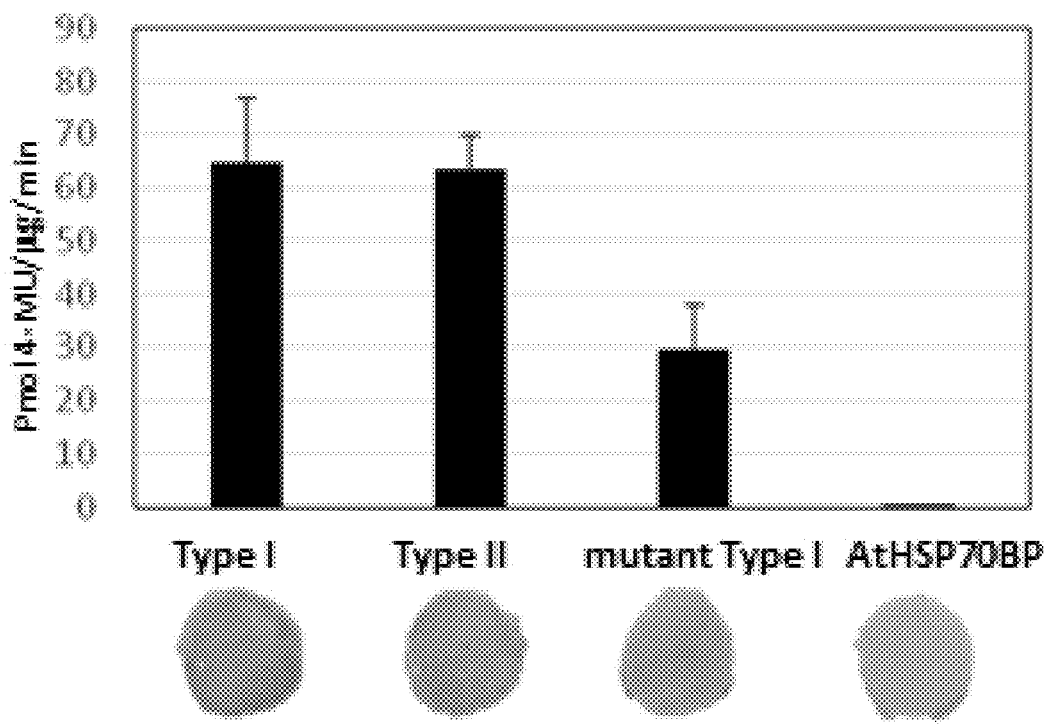

Four transgenic plants were treated with Xcc at the concentration of $5\times10^8$ CFU/ml. Typical canker symptoms were observed on the four independent transgenic lines similarly as the wild type control plants, at five days post inoculation (DPI) (FIG. 4a). No change in canker development was observed on #D18 and #D22, whose mutation rate on CsLOBP was 54.54% and 81.25%, respectively (Table 2). To test whether mutation of $EBE_{PthA4}$-Type I CsLOBP affects PthA4 activation of CsLOB1 gene, Type I CsLOBP, Type II CsLOBP and mutant Type I CsLOBP were placed upstream of the GUS reporter gene to form p1380-TI CsLOBP-GUSin, p1380-TII CsLOBP-GUSin and p1380-MTI CsLOBP-GUSin, respectively (FIG. 4b). Via Xcc-facilitated agroinfiltration, GUS expression was detected in constructs containing Type I CsLOBP, Type II CsLOBP and mutant Type I CsLOBP (FIG. 4c), whereas no GUS expression was detected in the leaves treated by p1380-AtHSP70BP-GUSin, a negative control. The results indicated that Xcc-derived PthA4 could activate Type I CsLOBP, Type II CsLOBP, and unexpectedly, mutant Type I CsLOBP, though the latter showed lower activity (FIG. 4c). The susceptibility of #D18 and #D22 to Xcc could be attributed to the fact that mutant Type I CsLOBP could be still activated by PthA4 upon Xcc infection to some extent (FIG. 4c), and Type II CsLOBP is intact (FIG. 3). The mutant Type I CsLOBP could be activated by PthA4 could be attributable to the fact that the 1 bp insertion happened after position 13 in the $EBE_{PthA4}$. Mutation of $EBE_{PthA4}$ in position 11 to 13 did not significantly affect the PthA4 recognition despite some slight reduction as indicated by GUS assay. AvrBs3 effector recognized $EBE_{AvrBs3}$ containing 1 bp insertion.

Figure 4D:
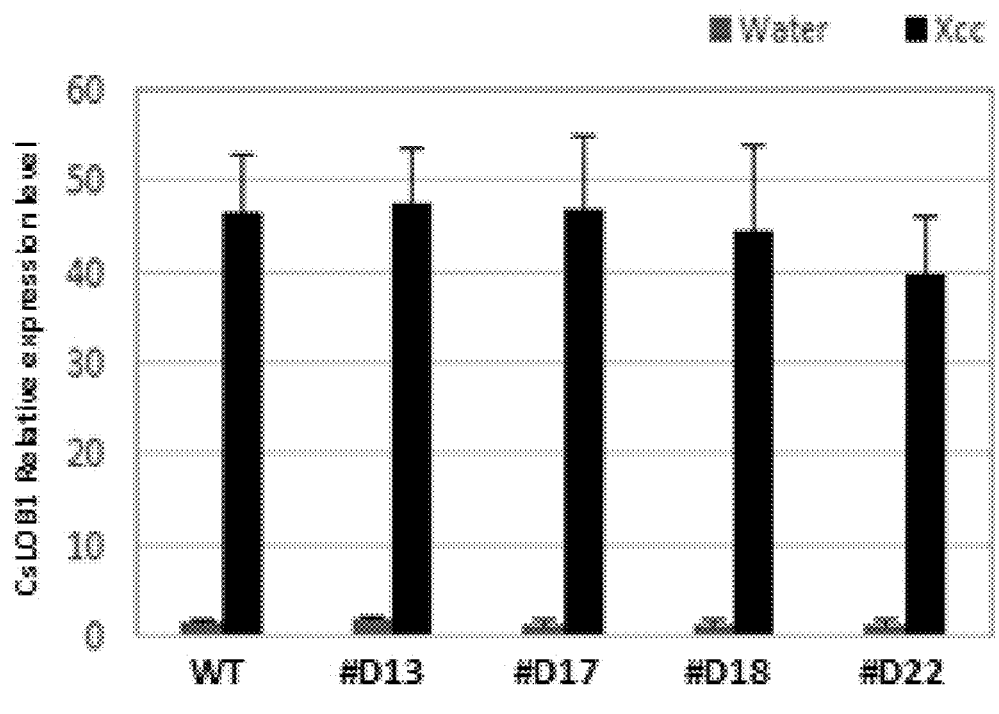

CsLOB1 expression level was dramatically elevated in wild type or transgenic Duncan plants upon Xcc infection. The expression level was slightly lower, but not significantly different, in #D18 and #D22 than in wild type (FIG. 4d). Therefore there were similar canker symptoms on transgenic plants and wild type Duncan grapefruit (FIG. 4a).

Example 5—Artificial dTALE dCsLOB1.3 Construct to Specifically Activate Type I CsLOBP Two artificial dTALEs, dCsLOB1.1 and dCsLOB1.2, were constructed to activate CsLOBP. The dCsLOB1.1 binding site is TAAAGCAGCTCCTCCTC (SEQ ID NO: 90) and the dCsLOB1.2 recognition sequence is TATAAACCCCTTTTGCCTT (SEQ ID NO: 91) (FIG. 7). A novel dTALE, dCsLOB1.3 was constructed (FIG. 5a), whose repeat variable diresidues (RVDs) correspond to a 18-nucleotide sequence 5'-CCTTTTGCCTTGAACTTT-3' (SEQ ID NO: 92) in the Type I CsLOBP (FIG. 7), whereas one nucleotide was missing or inserted in the Type II CsLOBP and the mutated Type I CsLOBP, respectively. dCsLOB1.3 was designed to activate Type I CsLOBP, but not Type II CsLOBP and mutant Type I CsLOBP. The dCsLOB1.3 binding sequence is preceded by a cytosine at position zero (FIG. 5a), which was reported to be applicable for dTALE activation. In addition, the RVD of dCsLOB1.3 located at 11 is NH, which was reported to be highly specific for guanine. As shown in FIG. 5b, dCsLOB1.3 was able to induce the GUS expression driven by Type I CsLOBP, however, no GUS expression was observed under the control of Type II CsLOBP or mutant Type I CsLOBP (FIG. 5b). Thus, dCsLOB1.3 specifically recognized Type I CsLOBP, but not Type II CsLOBP and the mutated Type I CsLOBP. The $11^{th}$-RVD-NH of dCsLOB1.3 could specifically recognize the 11th-guanine of 5'-CCTTTTGCCTTGAACTTT-3' (SEQ ID NO: 92, $1^{st}$ C counts as 0) in the Type I CsLOBP, but neither 11th-adenine of 5'-CCTTTTGCCTTAACTTT-3' (SEQ ID NO: 93, $1^{st}$ C counts as 0) in the Type II CsLOBP nor the $11^{th}$-thymine of 5'-CCTTTTTGCCTTGAACTTT-3' (SEQ ID NO: 94, $1^{st}$ C counts as 0) in the mutant Type I CsLOBP. Alternatively, the insertion or deletion site might be critical in affecting PthA4 or dTALE binding to their EBEs. Insertion or deletion causes frame shift. In reference to dTALE1.3, the deletion in Type II CsLOBP likely happens at the 11$^{th}$ nucleotide which abolishes the recognition of the downstream seven nucleotides. For mutant Type I CsLOBP, the insertion happens at position 6 which might abolish the recognition of downstream 12 nucleotides. Reduced, but not abolished PthA4 recognition of mutated type I CsLOBP (FIG. 4C) was observed. The 1 bp insertion in the mutant Type I CsLOBP happened after position 13 in the EBE$_{PthA4}$ which likely affected the downstream five nucleotides.

To further confirm that dCsLOB1.3 could specifically activate Type I CsLOBP, XccΔpthA4:dCsLOB1.3 was used to inoculate wild type Duncan grapefruit, Valencia sweet orange and pummelo. Five days post inoculation, canker symptoms were observed on Duncan grapefruit and Valencia sweet orange (FIG. 5c). However, XccΔpthA4:dCsLOB1.3 did not elicit citrus canker symptoms on pummelo (FIG. 5c). Pummelo contains Type II CsLOBP only whereas Valencia sweet orange contains only Type I CsLOBP and Duncan grapefruit contains both Type I and II CsLOBPs (FIG. 1a). Thus, upon Xcc infection, induction of one CsLOB1 allele was enough to induce canker development on Duncan (FIG. 5c).

Example 6—#D18 and #D22 Teansgenic Plants Alleviating XccΔpthA4:dCsLOB1.3 Infection Cas9/sgRNA:CsLOBP1-mediated mutations occurred mostly in somatic cells (FIG. 3d). Therefore, two kinds of somatic cells are supposed be present in transgenic Duncan: mutant somatic cells, which have mutated Type I CsLOBP and Type II CsLOBP, and wild type somatic cells, which contain wild type Type I CsLOBP and Type II CsLOBP. Since dCsLOB1.3 could not activate mutated Type I CsLOBP and Type II CsLOBP (FIG. 5), maybe because Cas9/sgRNA:CsLOBP1-transformed Duncan containing higher mutation rate in Type I CsLOBP has higher percentage of XccΔpthA4:dCsLOB1.3-resistant mutant somatic cell, resulting in alleviated canker symptoms upon XccΔpthA4:dCsLOB1.3 infection. The four transgenic lines of Duncan grapefruit plants were inoculated with XccΔpthA4:dCsLOB1.3. Typical canker symptoms were observed on transgenic plants #D13 and #D17 (FIG. 6a). In contrast, at 3 days post inoculation, no visible canker symptoms were present on #D18 and #D22. At 7 days post inoculation, weak canker symptoms on #D18 and no visible canker symptoms on #D22 were observed (FIG. 6b). The results indicated that #D18 and #D22, whose mutation rate was 54.54% and 81.25% respectively, had alleviated canker symptoms in the presence of XccΔpthA4:dCsLOB1.3.

Example 7—No Cas9/SGRNA:CsLOBP1-Mediated Off-Target Mutation in Transgenic Duncan Potential off-target mutagenesis mediated by Cas9/sgRNA:CsLOBP1 was analyzed in four Duncan transformants By employing a web tool (see world wide website: cbi.hzau.edu.cn/cgi-bin/CRISPR), eighty-five putative off-targets were found, from which 9 containing PAM were chosen for further sequencing analysis. Briefly, the 9 potential off-targets were PCR-amplified from transgenic Duncan plants using the corresponding primers (FIG. 8). After blunt end cloning, 8 random colonies for every potential off-target were selected for sequencing. The results indicated that no off-target mutation was detected (FIG. 8). However, since only 9 among 85 potential off-targets were subjected to sequencing analysis, the possibility of off-target mutagenesis of Cas9/sgRNA:CsLOBP in transgenic Duncan plants was not ruled out. Given that Duncan grapefruit whole genome is available, whole genome sequencing analysis can be employed to single out the off-targets in Duncan transformants once double mutants with biallelic mutations as described previously in *Arabidopsis* and rice are obtained (Feng et al., 2014; Zhang et al., 2014).

Example 8—Citrus Varieties Resistant to Xanthomonas Citri Infection

For bacterial pathogens containing TALEs, e.g., *Xanthomonas*, the disease susceptibility is determined by the interaction between the dominant TALE pathogenicity gene and the corresponding disease susceptibility gene in a gene-for-gene manner. TALEs contribute to pathogen virulence by transcriptionally activating specific disease susceptibility genes. PthA4 is the dominant pathogenicity gene of X, citri and is essential for inducing citrus canker symptoms. PthA4 has been known to induce gene expression of the susceptibility gene CsLOB1 leading to citrus canker. PthA4 binds to the EBE in the promoter region of CsLOB1 gene to activate its gene expression via a series of amino acid repeats in the coding central portion. Similarly, Os8N3 in *X. oryzae* pv. *oryzae* has been determined to be a host disease-susceptibility gene for bacterial blight of rice. The corresponding TALE for Os8N3 is PthXo1. Os11N3 (also called OsSWEET14) is another susceptibility gene for rice bacterial blight which is activated by AvrXa7 of X, oryzae pv. oryzae. Mutation of the EBEs in the promoter region of the susceptibility genes has been suggested to be an efficient approach to control the corresponding plant diseases. TALEN was used to modify the EBE of Os11N3 whereas Cas9/sgRNA was used in this study.

Figure 5A:
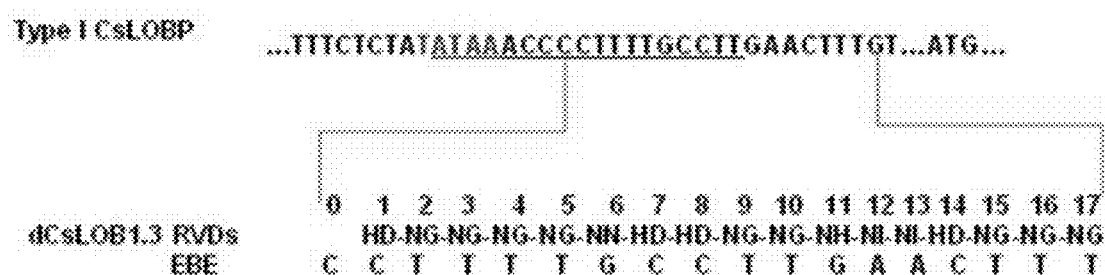
FIGS. 5a-5c. Artificial dTALE dCsLOB1.3 for Type I CsLOBP activation. (a) RVDs of artificial dTALE dCsLOB1.3 and the corresponding EBE sequence in host genome (SEQ ID NO: 108). $EBE_{PthA4}$-TI CsLOBP was underlined, red font represents putative TATAA box. Artificial dCsLOB1.3, binding to a sequence 7 bp downstream of $EBE_{pthA4}$-TI CsLOBP, was designed to specifically activate Type I CsLOBP, but not Type II CsLOBP or mutant Type I CsLOBP. (b) Via Xcc306ΔpthA4:dCsLOB1.3-facilitated agroinfiltration, quantitative GUS assay and GUS histochemical staining were performed to study the effects of Xcc-derived dCsLOB1.3 on CsLOBPs. As expected, GUS expression, only under the control of Type I CsLOBP, could be activated. The experiments were repeated twice with similar results. (c) In the presence of Xcc, citrus canker symptoms were observed on Duncan (containing Type I CsLOBP and Type II CsLOBP), Valencia (containing Type I CsLOBP) and pummelo (containing Type II CsLOBP) at 4 DPI, since PthA4 derived from Xcc could activate Type I CsLOBP and Type II CsLOBP. In the presence of Xcc306ΔpthA4:dCsLOB1.3, citrus canker symptoms were not observed on pummelo, since dCsLOB1.3 could not activate Type II CsLOBP, which is present in pummelo.
Figure 5B:
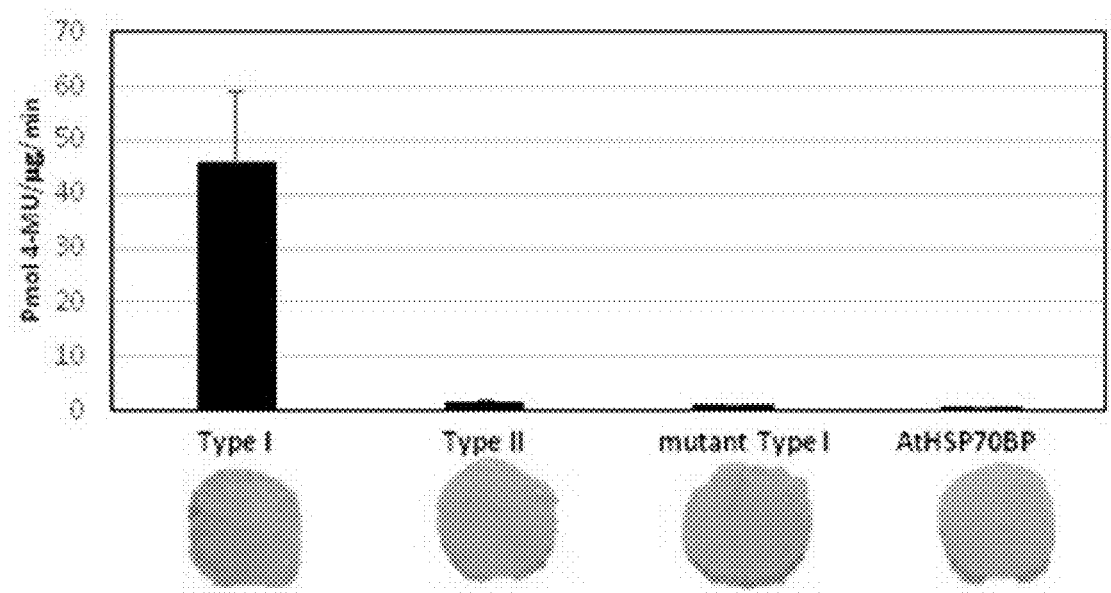
Figure 5C:
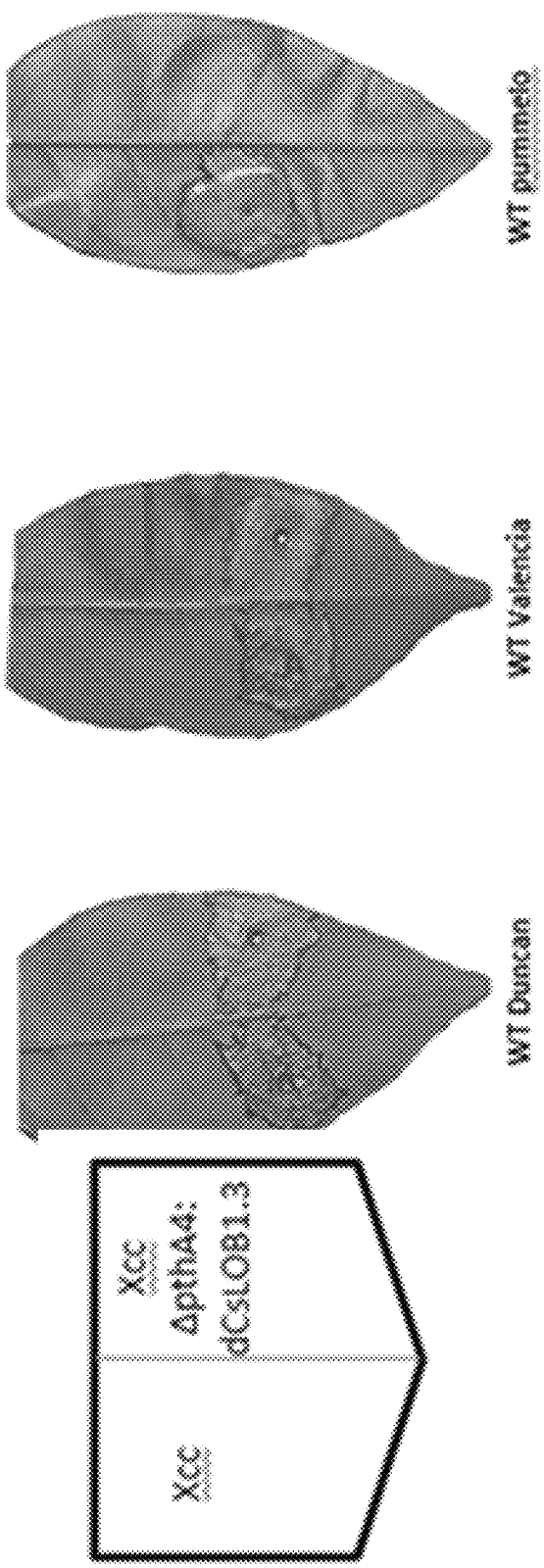
Figure 6A:
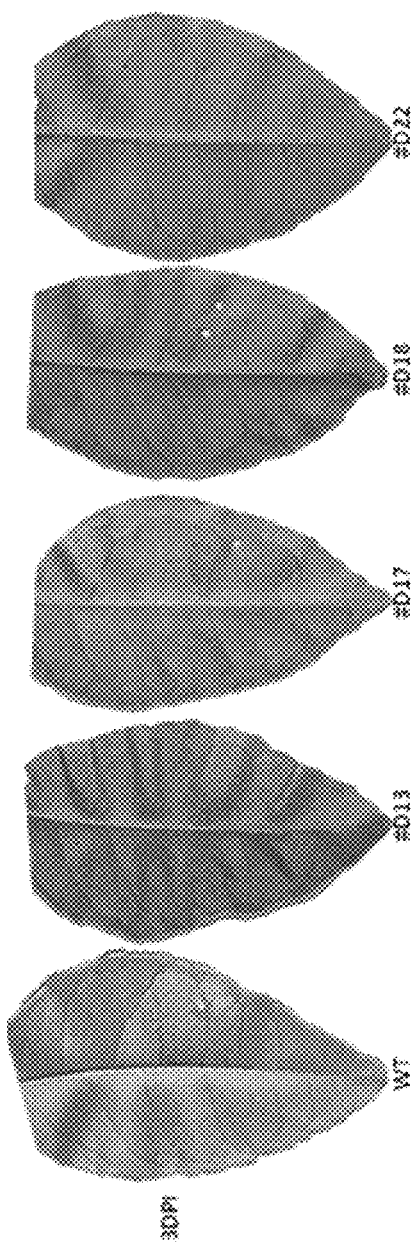
FIGS. 6a-6b. #D18 and #D22 resistant against Xcc306ΔpthA4:dCsLOB1.3. (a) At 3 days post inoculation with Xcc306ΔpthA4:dCsLOB1.3, there was no citrus canker symptoms on #D18 and #D22, whose $EBE_{pthA4}$-TI CsLOBP mutation rates were higher, whereas typical canker symptoms were observed on #D13 and #D17, which had lower mutant rates. Wild type Duncan grapefruit was used as a control. (b) At 7 days post inoculation with Xcc306ΔpthA4:dCsLOB1.3, weak canker symptom was detected on #D18, which was pointed out by an arrow. There was no citrus canker symptom on #D22, whose $EBE_{pthA4}$-TI CsLOBP mutant rate was highest among four transgenic plants. The results indicated that #D18 and #D22 could resist against Xcc306ΔpthA4:dCsLOB1.3.
Figure 6B:
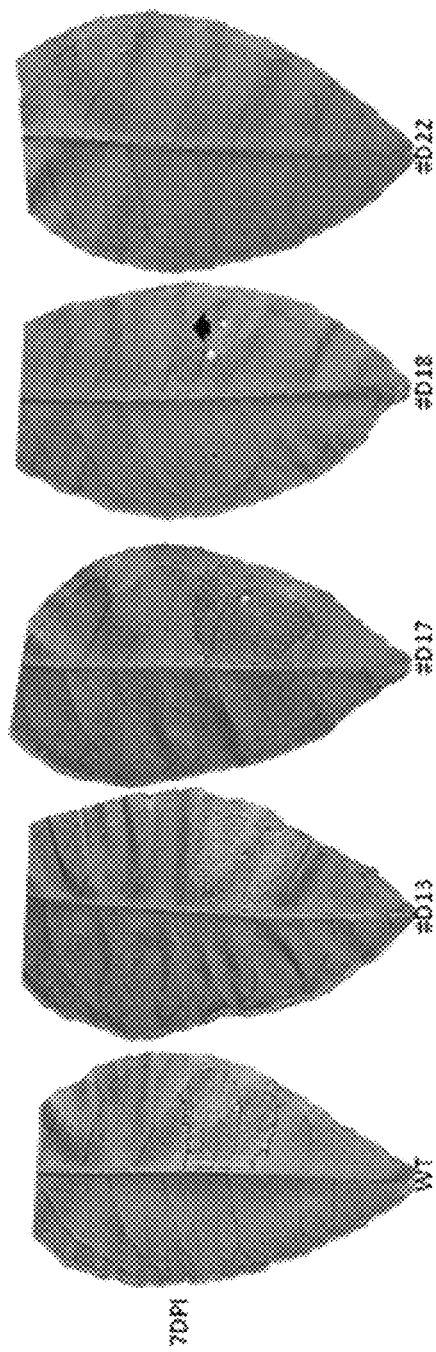

The EBE$_{PthA4}$ modified Duncan grapefruit did not show resistance against *X. citri* (FIG. 4a). This may be caused by three reasons. First, only Type I CsLOBP was mutated and Type II CsLOBP was intact in the EBE$_{PthA4}$ region of the four transgenic lines (FIGS. 1 and 3b). Second, only a proportion of Type I CsLOBP was successfully modified by Cas9/sgRNA:CsLOBP1 in transgenic plants, since Cas9/sgRNA:CsLOBP1-direction mutations took place mostly in somatic cells (FIG. 3d), which is similarly as Cas9/sgRNA-transformed *Arabidopsis*. Third, the mutated Type I CsLOBP could still be recognized by PthA4, though at lower activity as indicated by the lower GUS activity (FIG. 4c). Intriguingly, it has been reported that 1 bp insertion did not abolish the interaction between AvrBs3 and EBE$_{AvrBs3}$ either, though 2 bp or 3 bp insertion did in most cases. Therefore, it is likely that TALEs may tolerate some base pair change in its corresponding binding sequence. Actually, PthA4 could recognize both CsSWEET1 promoter and CsLOBP, and importantly, EBE$_{PthA4}$ in CsSWEET1 promoter is different from that of CsLOBP. However, it is unclear which base pair is unchangeable for maintaining TALEs-EBE interaction. Consequently, CsLOB1 expression could still be notably induced upon Xcc infection on transgenic Duncan plants, based on quantitative RT-PCR analysis (FIG. 4d), leading to similar canker symptoms on transgenic and wild type Duncan plants (FIG. 4a).

dCsLOB1.3 was designed to specifically activate Type I CsLOBP (FIGS. 5a and 5b). Wild type Duncan, containing one allele of Type I CsLOBP and another allele of Type II CsLOBP, could readily develop canker upon XccΔpthA4:dCsLOB1.3 infection (FIG. 5c). Pummelo only contains Type II CsLOBP which could not be recognized by dCsLOB1.3 (FIG. 5b) and showed resistance against XccΔpthA4:dCsLOB1.3 infection (FIG. 5c). Therefore, activation of a single allele of susceptibility gene is enough to induce plant disease and mutation of both alleles of CsLOBP is needed to generate citrus canker resistant plants. Consistently, monoallelic mutation in the EBE of Os11N3 in T0 rice plants did not affect the susceptibility to *X. oryzae* pv. *oryzae*. Biallelic mutations in the $EBE_{PthA4}$ of CsLOB1 of Duncan could generate resistant plant since two transgenic plants (#D18 and #D22) containing higher mutation rate of T1 CsLOBP and T2 CsLOBP, which could not be recognized by dCsLOB1.3, exhibited alleviated canker symptoms upon XccΔpthA4:dCsLOB1.3 infection (FIGS. 6a and b). The RVDS in dCsLOB1.3 could not recognize the two alleles, i.e., mutated Type I CsLOBP and Type II CsLOBP, in the transgenic Duncan plants (FIGS. 1 and 3). Consistently, dCsLOB1.3 could not induce the expression of mutated Type I CsLOBP and Type II CsLOBP 5b). Biallelic mutation for the CsLOBP can be generated in different varieties including sweet orange and Duncan grapefruit.

Cas9/sgRNA system was used to edit Duncan grapefruit genome via stable transformation. Activation of a single allele of susceptibility gene CsLOB1 is enough to induce citrus canker disease and mutation of both alleles of CsLOB1 is required to generate citrus canker resistant plants. Therefore, Cas9/sgRNA system provides a promising alternative method for citrus basic science and breeding.

Example 9—Generating Disease-Resistant Citrus Varieties Via Genome Editing in the Coding Region of CsLOB1 Gene Breeding disease resistant citrus varieties is a challenging task due to multiple limitations including polyembryony, and extended juvenility. CRISPR/Cas9/sgRNA is herein used to modify the canker susceptibility gene CsLOB1 to generate canker resistant citrus varieties. This approach provides resistant/tolerant citrus varieties against HLB, the most devastating disease threating the survival of citrus industry worldwide.

Citrus production faces many biotic and abiotic challenges. Among them, bacterial pathogens, Xcc and Candidatus Liberibacter asiaticus, responsible for citrus canker and HLB disease respectively, cause devastating effect on citrus production. Breeding disease-resistant varieties has long been deemed to be the most efficient and sustainable approach to control plant diseases. However, citrus breeding has often been hindered by polyembryony, pollen-ovule sterility, sexual and graft incompatibilities, and extended juvenility. This example uses CRISPR technology to edit a specific disease-susceptibility gene in citrus to generate canker resistant plant.

CsLOB1 is a critical citrus susceptibility gene for citrus canker. CsLOB1 is a member of the Lateral Organ Boundaries Domain (LBD) gene family of plant transcription factors and is directly targeted by virulence effectors of Xcc. All strains of Xcc encode a transcription activator-like (TAL) effector PthA that recognizes an effector binding element (EBE) in the promoter of CsLOB1 and induces gene expression. Furthermore, the EBEs of individual critical TAL effectors in various canker causing pathotypes, i.e., XccA, XccA*, XccA<sup>w</sup>, X. fuscans subsp. aurantifolii (Xfa) B and C, overlap. Thus, the EBE region of CsLOB1 presents an attractive target for genomic engineering of broad resistance to citrus canker. CsLOB1 gene is targeted using Cas9/sgRNA. The LBD family contains 34 members in citrus (see Worldwide Website: planttfdb.cbi.pku.edu.cn/family.php?sp=Csi&fam=LBD), 43 in *Arabidopsis* and 57 in poplar. LBD genes play important roles in plant growth and development. CsLOB1 function remains unknown in citrus. Genome modification has been employed to disrupt the EBE or coding region of susceptibility gene. To generate blight-resistant rice, the EBE region of OsSweet14, a susceptibility gene for PthXo3 of *X. oryzae* pv. *oryzae* (Xoo), was successfully modified using TALEN and the coding region of OsSweet13, a disease-susceptibility gene for PthXo2 of Xoo, was disrupted by Cas9/sgRNA. Here, the generation of canker resistant citrus by disrupting the coding region of CsLOB1 using Cas9/sgRNA is described.

Duncan grapefruit (Citrus x *paradisi*) is used as a model to conduct the genome editing since grapefruit is one of the most canker susceptible citrus varieties. Grapefruit contains two alleles of CsLOB1, Type I and Type II, since grapefruit is a hybrid of maternal donor pummelo (*C. maxima*) and paternal donor sweet orange (*C. sinensis*) (FIG. 11). The two alleles of CsLOB1 showed distinction at both nucleotide and protein levels. The sgRNA was selected to target a conserved region in both alleles (FIGS. 11-12). To facilitate the screen process, a binary vector GFP-p1380N-Cas9/sgRNA:cslob1 was constructed, which contains a GFP (FIG. 12). The GFP fluorescence allows for selection of plants containing GFP-p1380N-Cas9/sgRNA:cslob1. First, Xcc-facilitated agroinfiltration was used to test GFP-p1380N-Cas9/sgRNA:cslob1 function using transient expression in citrus leaves. Four days after agroinfiltration, GFP fluorescence was observed at the site agroinfiltrated with GFP-p1380N-Cas9/sgRNA:cslob1; whereas no GFP signal was observed at the site agroinfiltrated with p1380-AtHSP70BP-GUSin (FIG. 13A). Therefore, GFP reporter can be readily harnessed to single out transgenic shoots during *Agrobacterium*-mediated epicotyl transformation. Confirmation using amplification and sequencing showed that 15 among 100 colonies contained the targeted modification (FIGS. 13B-13C). Therefore, GFP-p1380N-Cas9/sgRNA:cslob1 is functional for CsLOB1 coding region targeting.

GFP-p1380N-Cas9/sgRNA:cslob1 was then used to modify CsLOB1 in Duncan grapefruit via *Agrobacterium*-mediated epicotyl transformation. Six independent transgenic lines, $D_{LOB}2$, $D_{LOB}3$, $D_{LOB}9$, $D_{LOB}10$, $D_{LOB}11$ and DLOB12, were successfully established, and verified by GFP and PCR analyses (FIGS. 9A-9B). To precisely calculate GFP-p1380N-Cas9/sgRNA:cslob1-mediated mutation efficiency and assess mutation genotype, targeted next-generation sequencing was conducted of the six transgenic lines after amplification using primers targeting a 380 bp region cover the mutated site. More than 50,000 paired-end reads were generated for each sample. After filtering and quality trimming, the remaining reads were grouped to clusters with a threshold of 100% pairwise identity using UCLUST. Based on the sequencing results, the mutation rate was calculated to be 31.58%, 23.80%, 89.36%, 88.79%, 46.91% and 51.12% for $D_{LOB}2$, $D_{LOB}3$, $D_{LOB}9$, $D_{LOB}10$, $D_{LOB}11$, and $D_{LOB}12$, respectively (FIG. 10A).

Figure 10B:
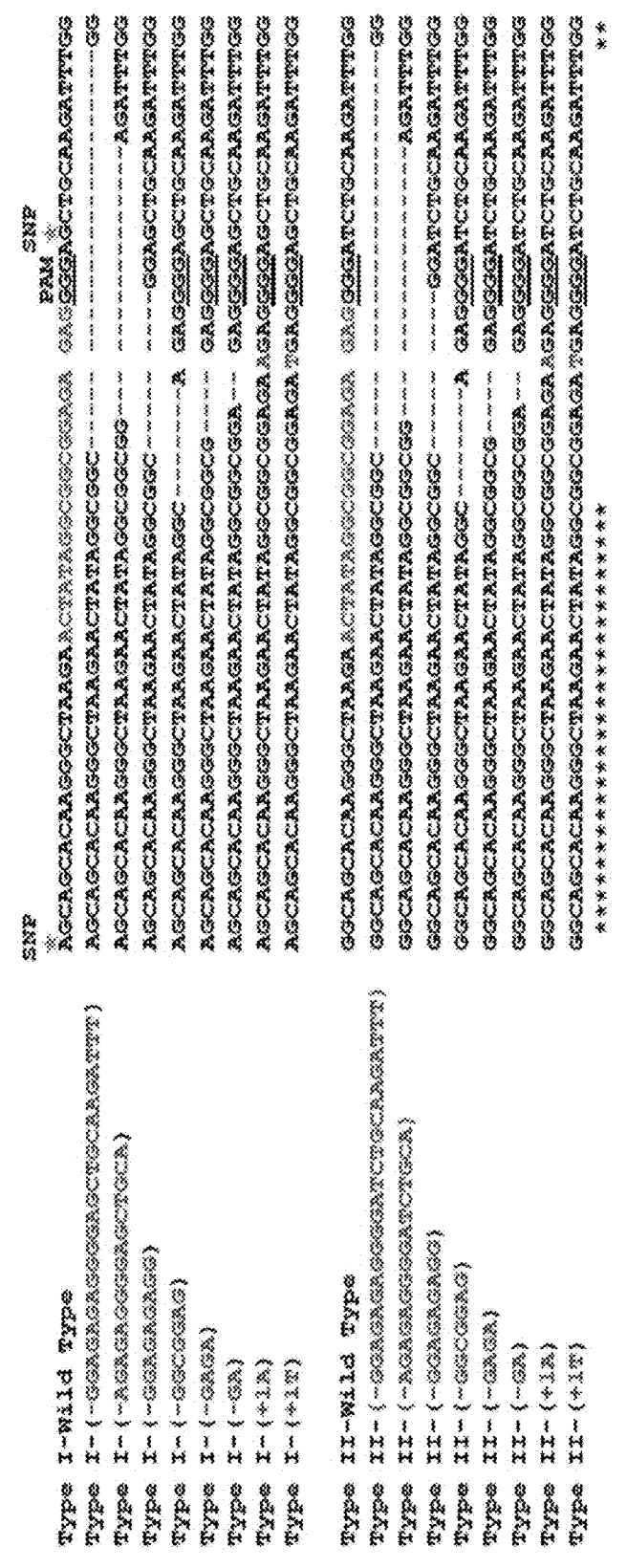

Similar mutation genotypes were observed in the six transgenic lines of Duncan grapefruit (Table 1). More than half of the mutations were 1 bp insertions of A or T, resulting in frame shift (FIG. 10B and Table 1). The majority of deletions were short, ranging from 2 bp to 22 bps. Most of 2 bp deletions were GA deletion (FIG. 10B and Table 1). The 1 bp insertions took place at the 4th bp upstream of the PAM site, so did GA deletion and GAGA deletion (FIG. 10B), which is consistent with the previous report that Cas9 nuclease cleaves target DNA at a position three base pairs upstream of the PAM sequence. Some short deletions, AGAGAGGGGA(G/T)CTGCA (SEQ ID NO: 23 and 32) and AGAGAGGGGA(G/T)CTGCAAGATTT (SEQ ID NO: 22 and 31), removed the PAM site (FIG. 10B). To confirm the next generation sequencing results, $D_{LOB}9$ and $D_{LOB}10$ were subjected to Sanger sequencing. Consequently, 10 among 11 colonies contained the GFP-p1380N-Cas9/sgRNA:cslob1-directed modification in $D_{LOB}9$, and so did 10 among 12 colonies in $D_{LOB}10$ (FIG. 14).

Figure 9C:
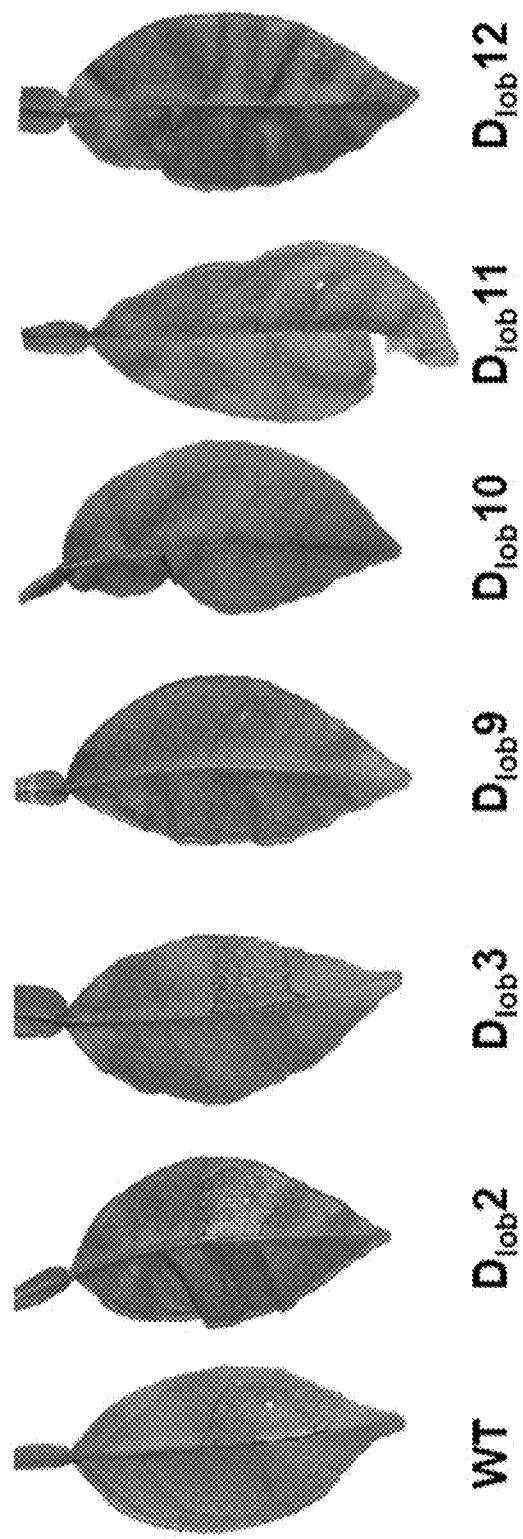

Susceptibility of the six CsLOB1 modified Duncan grapefruit plants was tested with Xcc at the concentration of $5\times10^8$ CFU/ml. $D_{LOB}2$ and $D_{LOB}3$ showed canker symptoms similar to wild type Duncan grapefruit. No canker symptoms were observed on $D_{LOB}9$, $D_{LOB}10$, $D_{LOB}11$ and DLOB12 at 4 DPI (FIG. 9C). However, canker symptoms were observed on $D_{LOB}9$, $D_{LOB}10$, $D_{LOB}11$ and $D_{LOB}12$ at 5 DPI even though at much reduced level compared to wild type grapefruit (FIG. 15). The canker symptoms of the CsLOB1 modified plants exhibit reverse correlation with mutation rate (FIGS. 9C and 10A, and FIG. 15). The appearance of the symptoms might result from wild type cells or mutants that could not abolish the CsLOB1 function. No visible phenotype change was observed for CsLOB1 edited grapefruit lines (FIG. 16).

Potential GFP-p 1380N-Cas9/sgRNA:cslob1-directed off-target mutagenesis were analyzed in Duncan grapefruit. The putative off-targets were identified as described by Lei et al. (2014). Seven putative off-targets were identified (FIG. 17). Amplification and Sanger sequencing were used to identify the putative off-target mutations. No off-target mutation was identified in the six CsLOB1 modified plants (FIG. 17). However, since only ten random colonies per putative off-target site were subjected to sequencing analysis, the possibility of off-target mutagenesis could not be ruled out.

Overall, this Example describes generation of canker resistant plants by modifying susceptibility genes. The initial screen of putative genome modified plants is aided with GFP. Similar approaches can be used to generate HLB resistant/tolerant citrus varieties by modifying genes involved in symptom development and targets of critical virulence factors of Ca. L. asiaticus.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Belhaj, K., Chaparro-Garcia, A., Kamoun, S., Patron, N. J. and Nekrasov, V. (2015) Editing plant genomes with CRISPR/Cas9. *Curr Opin Biotechnol* 32, 76-84. Boch, J. and Bonas, U. (2010) *Xanthomonas* AvrBs3 Family-type III effectors: discovery and function. *Annu Rev Phytopathol* 48, 419-436.
2. Bortesi, L. and Fischer, R. (2015) The CRISPR/Cas9 system for plant genome editing and beyond. *Biotechnol Adv* 33, 41-52.
3. Brooks, C., Nekrasov, V., Lippman, Z. B. and Van Eck, J. (2014) Efficient gene editing in tomato in the first generation using the clustered regularly interspaced short palindromic repeats/CRISPR-associated9 system. *Plant Physiol* 166, 1292-1297.
4. Cermak, T., Doyle, E. L., Christian, M., Wang, L., Zhang, Y., Schmidt, C., Bailer, J. A., Somia, N. V., Bogdanove, A. J. and Voytas, D. F. (2011) Efficient design and assembly of custom TALEN and other TAL effector-based constructs for DNA targeting. *Nucleic Acids Res* 39, e82.
5. Doudna, J. A. and Charpentier, E. (2014) Genome editing. The new frontier of genome engineering with CRISPR-Cas9. *Science* 346, 1258096.
6. Duan, Y., Castaneda, A., Zhao, G., Erdos, G. and Gabriel, D. (1999) Expression of a single, host-specific, bacterial pathogenicity gene in plant cells elicits division, enlargement, and cell death. *Molecular Plant-Microbe Interactions* 12, 556-560.
7. Durai, S., Mani, M., Kandavelou, K., Wu, J., Porteus, M. H. and Chandrasegaran, S. (2005) Zinc finger nucleases: custom-designed molecular scissors for genome engineering of plant and mammalian cells. *Nucleic Acids Res* 33, 5978-5990. Feng, Z., Mao, Y., Xu, N., Zhang, B., Wei, P., Yang, D. L., Wang, Z., Zhang, Z., Zheng, R., Yang, L., Zeng, L., Liu, X. and Zhu, J. K. (2014) Multigeneration analysis reveals the inheritance, specificity, and patterns of CRISPR/Cas-induced gene modifications in *Arabidopsis*. *Proc Natl Acad Sci USA* 111, 4632-4637.
8. Feng, Z., Zhang, B., Ding, W., Liu, X., Yang, D. L., Wei, P., Cao, F., Zhu, S, Zhang, F., Mao, Y. and Zhu, J. K. (2013) Efficient genome editing in plants using a CRISPR/Cas system. *Cell Res* 23, 1229-1232.
9. Gao, J., Wang, G., Ma, S., Xie, X., Wu, X., Zhang, X., Wu, Y., Zhao, P. and Xia, Q. (2015) CRISPR/Cas9-mediated targeted mutagenesis in *Nicotiana tabacum*. *Plant Mol Biol* 87, 99-110.
10. Gottwald, T., Hughes, G., Graham, J., Sun, X. and Riley, T. (2001) The citrus canker epidemic in Florida: the scientific basis of regulatory eradication policy for an invasive species. *Phytopathology* 91, 30-34.
11. Graham, J. H., Gottwald, T. R., Cubero, J. and Achor, D. S. (2004) *Xanthomonas axonopodis* pv. *citri*: factors affecting successful eradication of citrus canker. *Mol Plant Pathol* 5, 1-15.
12. Harrison, M. M., Jenkins, B. V., O'Connor-Giles, K. M. and Wildonger, J. (2014) A CRISPR view of development. *Genes Dev* 28, 1859-1872.
13. Hu, Y., Zhang, J., Jia, H., Sosso, D., Li, T., Frommer, W. B., Yang, B., White, F. F., Wang, N. and Jones, J. B. (2014) Lateral organ boundaries 1 is a disease susceptibility gene for citrus bacterial canker disease. *Proc Natl Acad Sci USA* 111, E521-529.
14. Jacobs, T. B., LaFayette, P. R., Schmitz, R. J. and Parrott, W. A. (2015) Targeted genome modifications in soybean with CRISPR/Cas9. *BMC Biotechnol* 15, 16.
15. Jia, H. and Wang, N. (2014a) Targeted Genome Editing of Sweet Orange Using Cas9/sgRNA. *PLoS One* 9, e93806.
16. Jia, H. and Wang, N. (2014b) Xcc-facilitated agroinfiltration of citrus leaves: a tool for rapid functional analysis of transgenes in citrus leaves. *Plant Cell Rep* 33, 1993-2001.
17. Jiang, W., Yang, B. and Weeks, D. P. (2014) Efficient CRISPR/Cas9-mediated gene editing in *Arabidopsis thaliana* and inheritance of modified genes in the T2 and T3 generations. *PLoS One* 9, e99225.
18. Jiang, W., Zhou, H., Bi, H., Fromm, M., Yang, B. and Weeks, D. P. (2013) Demonstration of CRISPR/Cas9/

18. sgRNA-mediated targeted gene modification in *Arabidopsis*, tobacco, sorghum and rice. *Nucleic Acids Res* 41, e188.
19. Jinek, M., Chylinski, K., Fonfara, I., Hauer, M., Doudna, J. A. and Charpentier, E. (2012) A programmable dual-RNA-guided DNA endonuclease in adaptive bacterial immunity. *Science* 337, 816-821.
20. Kumar, V. and Jain, M. (2015) The CRISPR-Cas system for plant genome editing: advances and opportunities. *J Exp Bot* 66, 47-57.
21. Lei, Y., Lu, L., Liu, H. Y., Li, S., Xing, F. and Chen, L. L. (2014) CRISPR-P: a web tool for synthetic single-guide RNA design of CRISPR-system in plants. *Mol Plant* 7, 1494-1496.
22. Li, J., Zhang, Y., Chen, K. L., Shan, Q. W., Wang, Y. P., Liang, Z. and Gao, C. X. (2013) [CRISPR/Cas: a novel way of RNA-guided genome editing]. *Yi Chuan* 35, 1265-1273.
23. Li, T., Liu, B., Spalding, M. H., Weeks, D. P. and Yang, B. (2012) High-efficiency TALEN-based gene editing produces disease-resistant rice. *Nat Biotechnol* 30, 390-392.
24. Liang, Z., Zhang, K., Chen, K. and Gao, C. (2014) Targeted mutagenesis in *Zea mays* using TALENs and the CRISPR/Cas system. *J Genet Genomics* 41, 63-68.
25. Liu, J., Li, C., Yu, Z., Huang, P., Wu, H., Wei, C., Zhu, N., Shen, Y., Chen, Y., Zhang, B., Deng, W. M. and Jiao, R. (2012) Efficient and specific modifications of the *Drosophila* genome by means of an easy TALEN strategy. *J Genet Genomics* 39, 209-215.
26. Livak, K. J. and Schmittgen, T. D. (2001) Analysis of relative gene expression data using real-time quantitative PCR and the method. *Methods* 25, 402-408.
27. Lloyd, A., Plaisier, C. L., Carroll, D. and Drews, G. N. (2005) Targeted mutagenesis using zinc-finger nucleases in *Arabidopsis. Proc Natl Acad Sci USA* 102, 2232-2237.
28. Mao, Y., Zhang, H., Xu, N., Zhang, B., Gou, F. and Zhu, J. K. (2013) Application of the CRISPR-Cas system for efficient genome engineering in plants. *Mol Plant* 6, 2008-2011.
29. Nekrasov, V., Staskawicz, B., Weigel, D., Jones, J. D. and Kamoun, S. (2013) Targeted mutagenesis in the model plant *Nicotiana benthamiana* using Cas9 RNA-guided endonuclease. *Nat Biotechnol* 31, 691-693.
30. Nishimasu, H., Ran, F. A., Hsu, P. D., Konermann, S., Shehata, S. I., Dohmae, N., Ishitani, R., Zhang, F. and Nureki, O. (2014) Crystal structure of Cas9 in complex with guide RNA and target DNA. *Cell* 156, 935-949.
31. Orbović, V. and Grosser, J. W. (2015) Citrus transformation using juvenile tissue explants. *Methods Mol Biol* 1224, 245-257.
32. Römer, P., Strauss, T., Hahn, S., Scholze, H., Morbitzer, R., Grau, J., Bonas, U. and Lahaye, T. (2009). Recognition of AvrBs3-like proteins is mediated by specific binding to promoters of matching pepper Bs3 alleles. *Plant Physiol* 150, 1697-1712.
33. Schreiber, T. and Bonas, U. (2014) Repeat 1 of TAL effectors affects target specificity for the base at position zero. *Nucleic Acids Res* 42, 7160-7169.
34. Shan, Q., Wang, Y., Li, J., Zhang, Y., Chen, K., Liang, Z., Zhang, K., Liu, J., Xi, J. J., Qiu, J. L. and Gao, C. (2013) Targeted genome modification of crop plants using a CRISPR-Cas system. *Nat Biotechnol* 31, 686-688.
35. Streubel. J., Blucher, C., Landgraf, A. and Both, J. (2012) TAL effector RVD specificities and efficiencies. *Nat Biotechnol* 30, 593-595,
36. Sun, X., Hu, Z., Chen, R., Jiang, Q., Song, G., Zhang H. and Xi, Y. (2015) Targeted mutagenesis in soybean using the CRISPR-Cas9 system. Sci Rep 5, 10342. Swarup, S., Yang, Y., Kingsley, M. and Gabriel, D. (1992) An *Xanthomonas citri* pathogenicity gene, pthA, pleiotropically encodes gratuitous avirulence on nonhosts. *Mol Plant Microbe Interact* 5, 204-213.
37. Upadhyay, S. K., Kumar, J., Alok, A. and Tuli, R. (2013) RNA-guided genome editing for target gene mutations in wheat. *G3 (Bethesda)* 3, 2233-2238.
38. Velasco, R. and Licciardello, C. (2014) A genealogy of the citrus family. *Nat Biotechnol* 32, 640-642.
39. Wu, G. A., Prochnik, S., Jenkins, J., Salse, J., Hellsten, U., Murat, F., Perrier, X., Ruiz, M., Scalabrin, S., Terol, J., Takita, M. A., Labadie, K., Poulain, J., Couloux, A., Jabbari, K., Cattonaro, F., Del Fabbro, C., Pinosio, S., Zuccolo, A., Chapman, J., Grimwood, J., Tadeo, F. R., Estornell, L. H., Muñoz-Sanz, J. V., Ibanez, V., Herrero-Ortega, A., Aleza, P., Pérez-Pérez, J., Ramón, D., Brunel, D., Luro, F., Chen, C., Farmerie, W. G., Desany, B., Kodira, C., Mohiuddin, M., Harkins, T., Fredrikson, K., Burns, P., Lomsadze, A., Borodovsky, M., Reforgiato, G., Freitas-Astúa, J., Quetier, F., Navarro, L., Roose, M., Wincker, P., Schmutz, J., Morgante, M., Machado, M. A., Talon, M., Jaillon, O., Ollitrault, P., Gmitter, F. and Rokhsar, D. (2014) Sequencing of diverse mandarin, pummelo and orange genomes reveals complex history of admixture during citrus domestication. *Nat Biotechnol* 32, 656-662.
40. Xie, K. and Yang, Y. (2013) RNA-guided Genome Editing in Plants Using A CRISPR-Cas System. *Mol Plant*.
41. Xu, Q., Chen, L. L., Ruan, X., Chen, D., Zhu, A., Chen, C., Bertrand, D., Jiao, W. B., Hao, B. H., Lyon, M. P., Chen, J., Gao, S., Xing, F., Lan, H., Chang, J. W., Ge, X., Lei, Y., Hu, Q., Miao, Y., Wang, L., Xiao, S., Biswas, M. K., Zeng, W., Guo, F., Cao, H., Yang, X., Xu, X. W., Cheng, Y. J., Xu, J., Liu, J. H., Luo, O. J., Tang, Z., Guo, W. W., Kuang, H., Zhang, H. Y., Roose, M. L., Nagarajan, N., Deng, X. X. and Ruan, Y. (2013) The draft genome of sweet orange (*Citrus sinensis*). *Nat Genet* 45, 59-66.
42. Yan, Q. and Wang, N. (2011) High-throughput screening and analysis of genes of *Xanthomonas citri* subsp. *citri* involved in citrus canker symptom development. *Mol Plant Microbe Interact*.
43. Yan, Q. and Wang, N. (2012) High-throughput screening and analysis of genes of *Xanthomonas citri* subsp. *citri* involved in citrus canker symptom development. *Mol Plant Microbe Interact* 25, 69-84.
44. Yang, B., Sugio, A. and White, F. F. (2006) Os8N3 is a host disease-susceptibility gene for bacterial blight of rice. *Proc Natl Acad Sci USA* 103, 10503-10508.
45. Zhang, H., Zhang, J., Wei, P., Zhang, B., Gou, F., Feng, Z., Mao, Y., Yang, L., Zhang, H., Xu, N. and Zhu, J. K. (2014) The CRISPR/Cas9 system produces specific and homozygous targeted gene editing in rice in one generation. *Plant Biotechnol J* 12, 797-807.
46. Zu, Y., Tong, X., Wang, Z., Liu, D., Pan, R., Li, Z., Hu, Y., Luo, Z., Huang, P., Wu, Q., Zhu, Z., Zhang, B. and Lin, S. (2013) TALEN-mediated precise genome modification by homologous recombination in zebrafish. *Nat Methods* 10, 329-331.
47. Dutt, M., Barthe, G., Irey, M. & Grosser, J. Transgenic Citrus Expressing an *Arabidopsis* NPR1 Gene Exhibit Enhanced Resistance against Huanglongbing (HLB; Citrus Greening). *PLoS One* 10, e0137134 (2015).

48. Fass, J. N. et al. Genome-Scale Analysis of Programmed DNA Elimination Sites in Tetrahymena *thermophila*. *G3 (Bethesda)* 1, 515-522 (2011).
49. Edgar, R. C. Search and clustering orders of magnitude faster than BLAST. *Bioinformatics* 26, 2460-2461 (2010).
50. Tamura, K., Stecher, G., Peterson, D., Filipski, A. & Kumar, S. MEGA6: Molecular Evolutionary Genetics Analysis version 6.0. *Mol Biol Evol* 30, 2725-2729 (2013).
51. Davey, M. R., Anthony, P., Power, J. B. & Lowe, K. C. Plant protoplasts: status and biotechnological perspectives. *Biotechnol Adv* 23, 131-171 (2005).
52. Shuai, B., Reynaga-Peña, C. G. & Springer, P. S. The lateral organ boundaries gene defines a novel, plant-specific gene family Plant Physiol 129, 747-761 (2002).
53. Yordanov, Y. S., Regan, S. & Busov, V. Members of the LATERAL ORGAN BOUNDARIES DOMAIN transcription factor family are involved in the regulation of secondary growth in *Populus*. Plant Cell 22, 3662-3677 (2010).
54. Husbands, A., Bell, E. M., Shuai, B., Smith, H. M. & Springer, P. S. LATERAL ORGAN BOUNDARIES defines a new family of DNA-binding transcription factors and can interact with specific bHLH proteins. Nucleic Acids Res 35, 6663-6671 (2007).
55. Thatcher, L. F., Kazan, K. & Manners, J. M. Lateral organ boundaries domain transcription factors: New roles in plant defense. Plant Signal Behav 7 (2012).
56. Xu, C., Luo, F. & Hochholdinger, F. LOB Domain Proteins: Beyond Lateral Organ Boundaries. Trends Plant Sci 21, 159-167 (2016).
57. Zhou, J. et al. Gene targeting by the TAL effector PthXo2 reveals cryptic resistance gene for bacterial blight of rice. Plant J (2015).
58. Jia, H., Orbovic, V., Jones, J. B. & Wang, N. Modification of the PthA4 effector binding elements in Type I CsLOB1 promoter using Cas9/sgRNA to produce transgenic Duncan grapefruit alleviating XccΔpthA4: dCsLOB1.3 infection. Plant Biotechnol J 14, 1291-1301 (2016).
59. Lei, Y. et al. CRISPR-P: a web tool for synthetic single-guide RNA design of CRISPR-system in plants. Mol Plant 7, 1494-1496 (2014).

We claim:

1. A citrus plant cell having one or more mutations in the promoters of both the alleles for CsLOB1 gene, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of the CsLOB1 genes.

2. The citrus plant cell of claim 1, wherein the plant cell is homozygous for CsLOB1 gene or heterozygous for CsLOB1 gene.

3. The citrus plant cell of claim 2, wherein the plant cell is heterozygous for CsLOB1 gene and the two alleles of CsLOB1 gene comprise CsLOB1 Type I and CsLOB1 Type II.

4. A citrus plant having one or more mutations in the promoters of both the alleles for CsLOB1 genes, wherein the one or more mutations are in the promoter binding sites for PthA4 protein from *Xanthomonas* spp., and wherein the one or more mutations reduce or abolish the binding of the *Xanthomonas* spp. PthA4 protein on to the binding sites in the promoters of the CsLOB1 genes.

5. The citrus plant of claim 4, wherein the plant is homozygous for CsLOB1 gene or heterozygous for CsLOB1 gene.

6. The citrus plant of claim 5, wherein the plant is heterozygous for CsLOB1 gene and the two alleles of CsLOB1 gene comprise CsLOB1 Type I and CsLOB1 Type II.

7. A seed of the citrus plant of claim 4, wherein the seed comprises the one or more mutations.

* * * * *

SEQUENCE LISTING

```
<160> NUMBER OF SEQ ID NOS: 110

<210> SEQ ID NO 1
<211> LENGTH: 19
<212> TYPE: DNA
<213> ORGANISM: Citrus sinensis

<400> SEQUENCE: 1
tataaacccc ttttgcctt                                                  19

<210> SEQ ID NO 2
<211> LENGTH: 19
<212> TYPE: DNA
<213> ORGANISM: Citrus sinensis

<400> SEQUENCE: 2
aaggcaaaag gggtttata                                                  19

<210> SEQ ID NO 3
<211> LENGTH: 25
<212> TYPE: DNA
<213> ORGANISM: Artificial Sequence
<220> FEATURE:
<223> OTHER INFORMATION: PCR primers for identifying potential
      off-targets

<400> SEQUENCE: 3
agacttgact tacgcactct tgtaa                                           25

<210> SEQ ID NO 4
<211> LENGTH: 25
<212> TYPE: DNA
<213> ORGANISM: Artificial Sequence
<220> FEATURE:
<223> OTHER INFORMATION: PCR primers for identifying potential
      off-targets

<400> SEQUENCE: 4
agtgctggtt tctagtgaaa cagtt                                           25

<210> SEQ ID NO 5
<211> LENGTH: 24
```

```
<212> TYPE: DNA
<213> ORGANISM: Artificial Sequence
<220> FEATURE:
<223> OTHER INFORMATION: PCR primers for identifying potential
      off-targets

<400> SEQUENCE: 5
actgagatca ttcatctcca tgat                                            24

<210> SEQ ID NO 6
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 6
tctgttggag acaaatcacc ggca                                            24

<210> SEQ ID NO 7
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 7
tgagaatgtc atggttgggg atga                                            24

<210> SEQ ID NO 8
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 8
acagcttcaa ggtagtcatt gcgt                                            24

<210> SEQ ID NO 9
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 9
atccatcatt tcaccacatg cctt                                            24

<210> SEQ ID NO 10
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 10
agaaatggaa acagcccatc aata                                            24

<210> SEQ ID NO 11
<211> LENGTH: 24
<212> TYPE: DNA
```

```
<213> ORGANISM: Artificial Sequence
<220> FEATURE:
<223> OTHER INFORMATION: PCR primers for identifying potential
      off-targets

<400> SEQUENCE: 11
tgcggacata ttgttacacc atat                                      24

<210> SEQ ID NO 12
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 12
actactaaga tggatcatag ccct                                      24

<210> SEQ ID NO 13
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 13
tggttagaga aatgttacgc tcaa                                      24

<210> SEQ ID NO 14
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 14
tgtgaggcat ttagatcaca gcct                                      24

<210> SEQ ID NO 15
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 15
taccatattg gaggcacatg cttt                                      24

<210> SEQ ID NO 16
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 16
tgggctcaac aatacggccc agtc                                      24

<210> SEQ ID NO 17
<211> LENGTH: 24
<212> TYPE: DNA
<213> ORGANISM: Artificial Sequence
```

```
<220> FEATURE:
<223> OTHER INFORMATION: PCR primers for identifying potential
      off-targets

<400> SEQUENCE: 17
attggcctaa gtcagaacgg taaa                                              24

<210> SEQ ID NO 18
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 18
tgaaagatca gtatgttcta ccat                                              24

<210> SEQ ID NO 19
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 19
accacttcag gcaactttcg caaa                                              24

<210> SEQ ID NO 20
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 20
tgcttgagtt tgagcacttg gggt                                              24

<210> SEQ ID NO 21
<211> LENGTH: 57
<212> TYPE: DNA
<213> ORGANISM: Citrus sinensis

<400> SEQUENCE: 21
agcagcacaa gggctaagaa ctataggcgg cggagagagg ggagctgcaa gatttgg          57

<210> SEQ ID NO 22
<211> LENGTH: 33
<212> TYPE: DNA
<213> ORGANISM: Artificial Sequence
<220> FEATURE:
<223> OTHER INFORMATION: Mutated Citrus sinensis sequence

<400> SEQUENCE: 22
agcagcacaa gggctaagaa ctataggcgg cgg                                    33

<210> SEQ ID NO 23
<211> LENGTH: 41
<212> TYPE: DNA
<213> ORGANISM: Artificial Sequence
<220> FEATURE:
<223> OTHER INFORMATION: Mutated Citrus sinensis sequence

<400> SEQUENCE: 23
```
agcagcacaa gggctaagaa ctataggcgg cggagatttg g                41

<210> SEQ ID NO 24
<211> LENGTH: 48
<212> TYPE: DNA
<213> ORGANISM: Artificial Sequence
<220> FEATURE:
<223> OTHER INFORMATION: Mutated Citrus sinensis sequence

<400> SEQUENCE: 24
agcagcacaa gggctaagaa ctataggcgg cggagctgca agatttgg         48

<210> SEQ ID NO 25
<211> LENGTH: 50
<212> TYPE: DNA
<213> ORGANISM: Artificial Sequence
<220> FEATURE:
<223> OTHER INFORMATION: Mutated Citrus sinensis sequence

<400> SEQUENCE: 25
agcagcacaa gggctaagaa ctataggcag aggggagctg caagatttgg       50

<210> SEQ ID NO 26
<211> LENGTH: 53
<212> TYPE: DNA
<213> ORGANISM: Artificial Sequence
<220> FEATURE:
<223> OTHER INFORMATION: Mutated Citrus sinensis sequence

<400> SEQUENCE: 26
agcagcacaa gggctaagaa ctataggcgg cggaggggag ctgcaagatt tgg   53

<210> SEQ ID NO 27
<211> LENGTH: 55
<212> TYPE: DNA
<213> ORGANISM: Artificial Sequence
<220> FEATURE:
<223> OTHER INFORMATION: Mutated Citrus sinensis sequence

<400> SEQUENCE: 27
agcagcacaa gggctaagaa ctataggcgg cggagagggg agctgcaaga tttgg   55

<210> SEQ ID NO 28
<211> LENGTH: 58
<212> TYPE: DNA
<213> ORGANISM: Artificial Sequence
<220> FEATURE:
<223> OTHER INFORMATION: Mutated Citrus sinensis sequence

<400> SEQUENCE: 28
agcagcacaa gggctaagaa ctataggcgg cggagaagag gggagctgca agatttgg   58

<210> SEQ ID NO 29
<211> LENGTH: 58
<212> TYPE: DNA
<213> ORGANISM: Artificial Sequence
<220> FEATURE:
<223> OTHER INFORMATION: Mutated Citrus sinensis sequence

<400> SEQUENCE: 29
agcagcacaa gggctaagaa ctataggcgg cggagatgag gggagctgca agatttgg   58

<210> SEQ ID NO 30
<211> LENGTH: 57
<212> TYPE: DNA
<213> ORGANISM: Citrus sinensis

<400> SEQUENCE: 30
ggcagcacaa gggctaagaa ctataggcgg cggagagagg ggatctgcaa gatttgg    57

<210> SEQ ID NO 31
<211> LENGTH: 33
<212> TYPE: DNA
<213> ORGANISM: Artificial Sequence
<220> FEATURE:
<223> OTHER INFORMATION: Mutated Citrus sinensis sequence

<400> SEQUENCE: 31
ggcagcacaa gggctaagaa ctataggcgg cgg    33

<210> SEQ ID NO 32
<211> LENGTH: 41
<212> TYPE: DNA
<213> ORGANISM: Artificial Sequence
<220> FEATURE:
<223> OTHER INFORMATION: Mutated Citrus sinensis sequence

<400> SEQUENCE: 32
ggcagcacaa gggctaagaa ctataggcgg cggagatttg g    41

<210> SEQ ID NO 33
<211> LENGTH: 48
<212> TYPE: DNA
<213> ORGANISM: Artificial Sequence
<220> FEATURE:
<223> OTHER INFORMATION: Mutated Citrus sinensis sequence

<400> SEQUENCE: 33
ggcagcacaa gggctaagaa ctataggcgg cggatctgca agatttgg    48

<210> SEQ ID NO 34
<211> LENGTH: 50
<212> TYPE: DNA
<213> ORGANISM: Artificial Sequence
<220> FEATURE:
<223> OTHER INFORMATION: Mutated Citrus sinensis sequence

<400> SEQUENCE: 34
ggcagcacaa gggctaagaa ctataggcag aggggatctg caagatttgg    50

<210> SEQ ID NO 35
<211> LENGTH: 53
<212> TYPE: DNA
<213> ORGANISM: Artificial Sequence
<220> FEATURE:
<223> OTHER INFORMATION: Mutated Citrus sinensis sequence

<400> SEQUENCE: 35
ggcagcacaa gggctaagaa ctataggcgg cggaggggat ctgcaagatt tgg    53

<210> SEQ ID NO 36
<211> LENGTH: 55
<212> TYPE: DNA
<213> ORGANISM: Artificial Sequence
<220> FEATURE:
<223> OTHER INFORMATION: Mutated Citrus sinensis sequence

<400> SEQUENCE: 36
ggcagcacaa gggctaagaa ctataggcgg cggagagggg atctgcaaga tttgg    55

<210> SEQ ID NO 37

```
<211> LENGTH: 58
<212> TYPE: DNA
<213> ORGANISM: Artificial Sequence
<220> FEATURE:
<223> OTHER INFORMATION: Mutated Citrus sinensis sequence

<400> SEQUENCE: 37
ggcagcacaa gggctaagaa ctataggcgg cggagaagag gggatctgca agatttgg      58

<210> SEQ ID NO 38
<211> LENGTH: 58
<212> TYPE: DNA
<213> ORGANISM: Artificial Sequence
<220> FEATURE:
<223> OTHER INFORMATION: Mutated Citrus sinensis sequence

<400> SEQUENCE: 38
ggcagcacaa gggctaagaa ctataggcgg cggagatgag gggatctgca agatttgg      58

<210> SEQ ID NO 39
<211> LENGTH: 731
<212> TYPE: DNA
<213> ORGANISM: Citrus paradisi

<400> SEQUENCE: 39
attgtcattc ttgcctttc cttttctctat ataaacccct tttgccttga actttgtttc      60
aactaaagca gctcctcctc atcccttact gtctttgctt tctcactaac tactacaacc    120
caacagtttt cttctctcaa aaatggaatg caaacacaaa attaatgtag caatcccaat    180
cactaatatg aagaacactc aattctcatc tccatctact ttctctactt ctcctccttc    240
tcaatcttct ccacgcttcc cttctcctaa tcatcaacaa ttgtcttctc cagaatcttc    300
tccaagcttt aaagcttctc cttcacaatc tctcccaaat cttgcagctc ccctctctcc    360
gccgcctata gttcttagcc cttgtgctgc ttgcaaaatc ctccgccgca gatgcgtcga    420
gaaatgtgtt ttagctccat attttccacc aaccgaacca tacaagttca ccattgctca    480
tagagtcttc ggtgctagca atatcatcaa gttcttgcag gtatgcactt cttttgtatg    540
tgataaattc aaactaatta aatgtccaac catttttttt ctaattggga gaaaaaaaa    600 acttgttaat tgttttattt tcatcaatta gttgtgtgat tagactttgg agtggttgat    660
tgttccactc tttttggaa acttacggac ttctctaatc aaaagaaaag agagtgtgac    720
atttcaactg a                                                       731

<210> SEQ ID NO 40
<211> LENGTH: 731
<212> TYPE: DNA
<213> ORGANISM: Citrus paradisi

<400> SEQUENCE: 40
attgtcattc ttgccttttc cttttctctat ataaacccct tttgccttaa ctttgtttca     60
actaaagcag ctcctcctca tcccttactg tcttcgcttt ctcactaact actacaaccc    120
aacagttttc ttctctcaaa aatggaatgc agacacaaaa ttaatgtagc aatcccaatc    180
attaatatga agaatactca attctcatct ccatctactt tctctacttc tcctccttct    240
caatcttctc catgcttcca ttctcctaat catcaacaat tgtcttctcc acaatcttct    300
ccaagcttta aagcttctcc ttcacaatct ctccaaatc ttgcagatcc cctctctccg     360
ccgcctatag ttcttagccc ttgtgctgcc tgcaaaatcc tccgccgcag atgcgtcgag    420
aaatgtgttt tagctccata ttttccacca accgaaccat acaagttcac cattgctcat    480
```

```
agggtcttcg gtgcaagcaa tatcatcaag ttcttgcagg tatgcacttc ttttgtatgt    540
gataaattca aactaattaa atgtccaacc attttttttt ctaattggga gaaaaaaaaa    600
acttgttaat tgttttattt tcatcaatta gttgtgtgat tagactttgg agtggttgat    660
tgttccactc tttttggaa acttacggac ttctctaatc aaaagaaaag agagtgtgac    720
atttcaactg a                                                         731
```

<210> SEQ ID NO 41
<211> LENGTH: 23
<212> TYPE: DNA
<213> ORGANISM: Artificial sequence
<220> FEATURE:
<223> OTHER INFORMATION: twenty nucleotides of target sequence
      conjugated to PAM sequence, GGG

<400> SEQUENCE: 41

```
actataggcg gcggagagag ggg                                             23
```

<210> SEQ ID NO 42
<211> LENGTH: 43
<212> TYPE: DNA
<213> ORGANISM: Artificial Sequence
<220> FEATURE:
<223> OTHER INFORMATION: mutated Citrus sinensis sequence

<400> SEQUENCE: 42

```
agggctaaga actataggcg gcggagagag gggatctgca aga                       43
```

<210> SEQ ID NO 43
<211> LENGTH: 41
<212> TYPE: DNA
<213> ORGANISM: Artificial Sequence
<220> FEATURE:
<223> OTHER INFORMATION: mutated Citrus sinensis sequence

<400> SEQUENCE: 43

```
agggctaaga actataggcg gcggagaggg gatctgcaag a                         41
```

<210> SEQ ID NO 44
<211> LENGTH: 44
<212> TYPE: DNA
<213> ORGANISM: Artificial Sequence
<220> FEATURE:
<223> OTHER INFORMATION: mutated Citrus sinensis sequence

<400> SEQUENCE: 44

```
agggctaaga actataggcg gcggagaaga ggggatctgc aaga                      44
```

<210> SEQ ID NO 45
<211> LENGTH: 44
<212> TYPE: DNA
<213> ORGANISM: Artificial Sequence
<220> FEATURE:
<223> OTHER INFORMATION: mutated Citrus sinensis sequence

<400> SEQUENCE: 45

```
agggctaaga actataggcg gcggagatga ggggagctgc aaga                      44
```

<210> SEQ ID NO 46
<211> LENGTH: 39
<212> TYPE: DNA
<213> ORGANISM: Artificial Sequence
<220> FEATURE:
<223> OTHER INFORMATION: mutated Citrus sinensis sequence

```
<400> SEQUENCE: 46
agggctaaga actataggcg gcggagggga gctgcaaga                    39

<210> SEQ ID NO 47
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 47
tgggcatcct aaagtaaagt agaa                                    24

<210> SEQ ID NO 48
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 48
acctagagct tctacattga atca                                    24

<210> SEQ ID NO 49
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 49
agttgttacc cgttacagcg gctg                                    24

<210> SEQ ID NO 50
<211> LENGTH: 25
<212> TYPE: DNA
<213> ORGANISM: Artificial Sequence
<220> FEATURE:
<223> OTHER INFORMATION: PCR primers for identifying potential
      off-targets

<400> SEQUENCE: 50
tgcttgaaga tcctcttcaa ttccc                                   25

<210> SEQ ID NO 51
<211> LENGTH: 25
<212> TYPE: DNA
<213> ORGANISM: Artificial Sequence
<220> FEATURE:
<223> OTHER INFORMATION: PCR primers for identifying potential
      off-targets

<400> SEQUENCE: 51
agcggcacga aatggtacgt ctcga                                   25

<210> SEQ ID NO 52
<211> LENGTH: 24
<212> TYPE: DNA
<213> ORGANISM: Artificial Sequence
<220> FEATURE:
<223> OTHER INFORMATION: PCR primers for identifying potential
      off-targets
```

```
<400> SEQUENCE: 52
acgaatagcc ttgggccact tcac                                          24

<210> SEQ ID NO 53
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 53
agaaagagaa gtgatgggaa agat                                          24

<210> SEQ ID NO 54
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 54
acatgccgaa tagaggaaac ggtg                                          24

<210> SEQ ID NO 55
<211> LENGTH: 25
<212> TYPE: DNA
<213> ORGANISM: Artificial Sequence
<220> FEATURE:
<223> OTHER INFORMATION: PCR primers for identifying potential
      off-targets

<400> SEQUENCE: 55
agctagcgcg tcgaattgat ttctg                                         25

<210> SEQ ID NO 56
<211> LENGTH: 25
<212> TYPE: DNA
<213> ORGANISM: Artificial Sequence
<220> FEATURE:
<223> OTHER INFORMATION: PCR primers for identifying potential
      off-targets

<400> SEQUENCE: 56
aggcagctct tcttctcctt attgc                                         25

<210> SEQ ID NO 57
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 57
agtcaacaac gatacaccca gcag                                          24

<210> SEQ ID NO 58
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 58
```
ttctctgagt atcagcccta tcag                    24

<210> SEQ ID NO 59
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 59
tgtgcgtcag gtccaaggaa ggtt                    24

<210> SEQ ID NO 60
<211> LENGTH: 24
<212> TYPE: DNA
<213> ORGANISM: Artificial Sequence
<220> FEATURE:
<223> OTHER INFORMATION: PCR primers for identifying potential
      off-targets

<400> SEQUENCE: 60
tggagcttcc tagcatagga gaag                    24

<210> SEQ ID NO 61
<211> LENGTH: 34
<212> TYPE: DNA
<213> ORGANISM: Artificial Sequence
<220> FEATURE:
<223> OTHER INFORMATION: primer for amplification of CaMV 35S promoter

<400> SEQUENCE: 61
actcgagact agtaccatgg tggactcctc ttaa         34

<210> SEQ ID NO 62
<211> LENGTH: 34
<212> TYPE: DNA
<213> ORGANISM: Artificial Sequence
<220> FEATURE:
<223> OTHER INFORMATION: primer for amplification of CaMV 35S promoter

<400> SEQUENCE: 62
aactttgttt ccctctccaa atgaaatgaa cttc         34

<210> SEQ ID NO 63
<211> LENGTH: 31
<212> TYPE: DNA
<213> ORGANISM: Artificial Sequence
<220> FEATURE:
<223> OTHER INFORMATION: primer for amplification of sgRNA-NosT fragment

<400> SEQUENCE: 63
caaggcaaag ttttagagct agaaatagca a            31

<210> SEQ ID NO 64
<211> LENGTH: 37
<212> TYPE: DNA
<213> ORGANISM: Artificial Sequence
<220> FEATURE:
<223> OTHER INFORMATION: primer for amplification of sgRNA-NosT fragment

<400> SEQUENCE: 64
acctgggccc ggcgcgccga tctagtaaca tagatga      37

<210> SEQ ID NO 65

```
<211> LENGTH: 29
<212> TYPE: DNA
<213> ORGANISM: Artificial Sequence
<220> FEATURE:
<223> OTHER INFORMATION: forward primer

<400> SEQUENCE: 65
aggtaagctt tctctatata aacccctttt                                      29

<210> SEQ ID NO 66
<211> LENGTH: 35
<212> TYPE: DNA
<213> ORGANISM: Artificial Sequence
<220> FEATURE:
<223> OTHER INFORMATION: forward primer

<400> SEQUENCE: 66
acctggatcc ttttgagaga agaaaactgt tgggt                                35

<210> SEQ ID NO 67
<211> LENGTH: 29
<212> TYPE: DNA
<213> ORGANISM: Artificial Sequence
<220> FEATURE:
<223> OTHER INFORMATION: Primer for amplification of CaMV 35S promoter

<400> SEQUENCE: 67
tatagtcctc tccaaatgaa atgaacttc                                       29

<210> SEQ ID NO 68
<211> LENGTH: 36
<212> TYPE: DNA
<213> ORGANISM: Artificial Sequence
<220> FEATURE:
<223> OTHER INFORMATION: Primer for amplification of sgRNA-NosT fragment

<400> SEQUENCE: 68
ggcggcggag agaggtttta gagctagaaa tagcaa                               36

<210> SEQ ID NO 69
<211> LENGTH: 44
<212> TYPE: DNA
<213> ORGANISM: Artificial Sequence
<220> FEATURE:
<223> OTHER INFORMATION: Primer for amplification of CaMV 35S terminator

<400> SEQUENCE: 69
aggtggatcc gagctcgaaa atttctccat aataatgtgt gagt                      44

<210> SEQ ID NO 70
<211> LENGTH: 39
<212> TYPE: DNA
<213> ORGANISM: Artificial Sequence
<220> FEATURE:
<223> OTHER INFORMATION: Primer for amplification of CaMV 35S terminator

<400> SEQUENCE: 70
aggtattaat aagcttcggg ggatctggat tttagtact                            39

<210> SEQ ID NO 71
<211> LENGTH: 47
<212> TYPE: DNA
<213> ORGANISM: Artificial Sequence
<220> FEATURE:
<223> OTHER INFORMATION: primer for amplification of cassava vein mosaic
      virus promoter
```

<400> SEQUENCE: 71
aggtactagt aagcttgcat gcccgcgcca gaaggtaatt atccaag    47

<210> SEQ ID NO 72
<211> LENGTH: 32
<212> TYPE: DNA
<213> ORGANISM: Artificial Sequence
<220> FEATURE:
<223> OTHER INFORMATION: primer for amplification of cassava vein mosaic
     virus promoter

<400> SEQUENCE: 72
aggtgtcgac aaacttacaa atttctctga ag    32

<210> SEQ ID NO 73
<211> LENGTH: 32
<212> TYPE: DNA
<213> ORGANISM: Artificial Sequence
<220> FEATURE:
<223> OTHER INFORMATION: primer for amplification of GFP fragment

<400> SEQUENCE: 73
aggtctcgag atgaagacta atcttttct ct    32

<210> SEQ ID NO 74
<211> LENGTH: 30
<212> TYPE: DNA
<213> ORGANISM: Artificial Sequence
<220> FEATURE:
<223> OTHER INFORMATION: primer for amplification of GFP fragment

<400> SEQUENCE: 74
tcgagctctt aaagctcatc atgtttgtat    30

<210> SEQ ID NO 75
<211> LENGTH: 26
<212> TYPE: DNA
<213> ORGANISM: Artificial Sequence
<220> FEATURE:
<223> OTHER INFORMATION: primer for amplification of CsLOB1 promoter and
     its coding region

<400> SEQUENCE: 75
attgtcattc ttgccttttc ctttct    26

<210> SEQ ID NO 76
<211> LENGTH: 24
<212> TYPE: DNA
<213> ORGANISM: Artificial Sequence
<220> FEATURE:
<223> OTHER INFORMATION: primer for amplification of CsLOB1 promoter and
     its coding region

<400> SEQUENCE: 76
tcagttgaaa tgtcacactc tctt    24

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
tgagcaatgg tgaacttgta tggttc    26

```
<210> SEQ ID NO 78
<211> LENGTH: 22
<212> TYPE: DNA
<213> ORGANISM: Artificial Sequence
<220> FEATURE:
<223> OTHER INFORMATION: Primer

<400> SEQUENCE: 78
attgaacaag atggattgca cg                                              22

<210> SEQ ID NO 79
<211> LENGTH: 24
<212> TYPE: DNA
<213> ORGANISM: Artificial Sequence
<220> FEATURE:
<223> OTHER INFORMATION: Primer

<400> SEQUENCE: 79
ttcgggggat ctggatttta gtac                                            24

<210> SEQ ID NO 80
<211> LENGTH: 21
<212> TYPE: DNA
<213> ORGANISM: Artificial Sequence
<220> FEATURE:
<223> OTHER INFORMATION: Primer

<400> SEQUENCE: 80
atcaaaggcc atggagtcaa a                                               21

<210> SEQ ID NO 81
<211> LENGTH: 21
<212> TYPE: DNA
<213> ORGANISM: Artificial Sequence
<220> FEATURE:
<223> OTHER INFORMATION: Primer

<400> SEQUENCE: 81
ttgtcgtttc ccgccttcag t                                               21

<210> SEQ ID NO 82
<211> LENGTH: 26
<212> TYPE: DNA
<213> ORGANISM: Artificial Sequence
<220> FEATURE:
<223> OTHER INFORMATION: Primer

<400> SEQUENCE: 82
tctcactaac tactacaacc caacag                                          26

<210> SEQ ID NO 83
<211> LENGTH: 35
<212> TYPE: DNA
<213> ORGANISM: Artificial Sequence
<220> FEATURE:
<223> OTHER INFORMATION: Primer

<400> SEQUENCE: 83
aggtaagctt attcatatta acgttatcaa tgatt                                35

<210> SEQ ID NO 84
<211> LENGTH: 24
<212> TYPE: DNA
<213> ORGANISM: Artificial Sequence
<220> FEATURE:
<223> OTHER INFORMATION: Primer
```

```
<400> SEQUENCE: 84
cgtcattcaa ttaaaattaa tgac                                         24

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
tccaccaacc gaaccataca                                              20

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
ggcacttgct tcatagacca t                                            21

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
gtaaccaagt ctgctgccaa g                                            21

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
gacccaaaca cccaacacat t                                            21

<210> SEQ ID NO 89
<211> LENGTH: 20
<212> TYPE: DNA
<213> ORGANISM: Citrus sinensis

<400> SEQUENCE: 89
gaaacaaagt tcaaggcaaa                                              20

<210> SEQ ID NO 90
<211> LENGTH: 17
<212> TYPE: DNA
<213> ORGANISM: Artificial Sequence
<220> FEATURE:
<223> OTHER INFORMATION: Primer

<400> SEQUENCE: 90
taaagcagct cctcctc                                                 17

<210> SEQ ID NO 91
<211> LENGTH: 19
<212> TYPE: DNA
```

```
<213> ORGANISM: Artificial Sequence
<220> FEATURE:
<223> OTHER INFORMATION: Primer

<400> SEQUENCE: 91
tataaacccc ttttgcctt                                               19

<210> SEQ ID NO 92
<211> LENGTH: 18
<212> TYPE: DNA
<213> ORGANISM: Artificial Sequence
<220> FEATURE:
<223> OTHER INFORMATION: Primer

<400> SEQUENCE: 92
ccttttgcct tgaacttt                                                18

<210> SEQ ID NO 93
<211> LENGTH: 17
<212> TYPE: DNA
<213> ORGANISM: Artificial Sequence
<220> FEATURE:
<223> OTHER INFORMATION: Primer

<400> SEQUENCE: 93
ccttttgcct taacttt                                                 17

<210> SEQ ID NO 94
<211> LENGTH: 19
<212> TYPE: DNA
<213> ORGANISM: Artificial Sequence
<220> FEATURE:
<223> OTHER INFORMATION: Primer

<400> SEQUENCE: 94
cctttttgcc ttgaacttt                                               19

<210> SEQ ID NO 95
<211> LENGTH: 55
<212> TYPE: DNA
<213> ORGANISM: Citrus sinensis

<400> SEQUENCE: 95
aggagctgct ttagttgaaa caaagttcaa ggcaaaaggg gtttatatag agaaa       55

<210> SEQ ID NO 96
<211> LENGTH: 54
<212> TYPE: DNA
<213> ORGANISM: Citrus sinensis

<400> SEQUENCE: 96
aggagctgct ttagttgaaa caaagttaag gcaaaagggg tttatataga gaaa        54

<210> SEQ ID NO 97
<211> LENGTH: 51
<212> TYPE: DNA
<213> ORGANISM: Citrus sinensis

<400> SEQUENCE: 97
tcctttctct atataaaccc cttttgcctt gaactttgtt tcaactaaag c           51

<210> SEQ ID NO 98
<211> LENGTH: 51
<212> TYPE: DNA
<213> ORGANISM: Artificial Sequence
```

```
<220> FEATURE:
<223> OTHER INFORMATION: SgRNA designed to target effector binding
      elements

<400> SEQUENCE: 98
aggaaagaga tatatttggg gaaaacggaa cttgaaacaa agttgatttc g        51

<210> SEQ ID NO 99
<211> LENGTH: 21
<212> TYPE: DNA
<213> ORGANISM: Artificial Sequence
<220> FEATURE:
<223> OTHER INFORMATION: SgRNA designed to target effector binding
      elements

<400> SEQUENCE: 99
gaaacaaagt tcaaggcaaa a                                         21

<210> SEQ ID NO 100
<211> LENGTH: 56
<212> TYPE: DNA
<213> ORGANISM: Artificial Sequence
<220> FEATURE:
<223> OTHER INFORMATION: Mutated Citrus sinensis sequence

<400> SEQUENCE: 100
aggagctgct ttagttgaaa caaagttcaa ggcaaaaagg ggtttatata gagaaa    56

<210> SEQ ID NO 101
<211> LENGTH: 56
<212> TYPE: DNA
<213> ORGANISM: Artificial Sequence
<220> FEATURE:
<223> OTHER INFORMATION: Mutated Citrus sinensis sequence

<400> SEQUENCE: 101
aggagctgct ttagttgaaa caaagttcaa ggcaaaaagg ggtttatata gagaaa    56

<210> SEQ ID NO 102
<211> LENGTH: 56
<212> TYPE: DNA
<213> ORGANISM: Artificial Sequence
<220> FEATURE:
<223> OTHER INFORMATION: Mutated Citrus sinensis sequence

<400> SEQUENCE: 102
aggagctgct ttagttgaaa caaagttcaa ggctaaaagg ggtttatata gagaaa    56

<210> SEQ ID NO 103
<211> LENGTH: 40
<212> TYPE: DNA
<213> ORGANISM: Citrus sinensis

<400> SEQUENCE: 103
cctttctcta tataaacccc ttttgccttg aactttgttt                      40

<210> SEQ ID NO 104
<211> LENGTH: 40
<212> TYPE: DNA
<213> ORGANISM: Artificial Sequence
<220> FEATURE:
<223> OTHER INFORMATION: mutated Citrus sinensis sequence

<400> SEQUENCE: 104
cctttctcta tataaacccc ttttgccttg aactttgttt                      40
```

<210> SEQ ID NO 105
<211> LENGTH: 40
<212> TYPE: DNA
<213> ORGANISM: Artificial Sequence
<220> FEATURE:
<223> OTHER INFORMATION: mutated Citrus sinensis sequence

<400> SEQUENCE: 105
cctttctcta tataaacccc ttttgccttg aactttgttt                    40

<210> SEQ ID NO 106
<211> LENGTH: 41
<212> TYPE: DNA
<213> ORGANISM: Artificial Sequence
<220> FEATURE:
<223> OTHER INFORMATION: mutated Citrus sinensis sequence

<400> SEQUENCE: 106
cctttctcta tataaacccc tttttgcctt gaactttgtc t                  41

<210> SEQ ID NO 107
<211> LENGTH: 41
<212> TYPE: DNA
<213> ORGANISM: Artificial Sequence
<220> FEATURE:
<223> OTHER INFORMATION: mutated Citrus sinensis sequence

<400> SEQUENCE: 107
cctttctcta tataaacccc tttttgccta gaattttgtc t                  41

<210> SEQ ID NO 108
<211> LENGTH: 36
<212> TYPE: DNA
<213> ORGANISM: Citrus sinensis

<400> SEQUENCE: 108
tttctctata taaacccctt ttgccttgaa ctttgt                        36

<210> SEQ ID NO 109
<211> LENGTH: 409
<212> TYPE: DNA
<213> ORGANISM: Citrus paradisi

<400> SEQUENCE: 109
attcatatta acgttatcaa tgatttttt ttaatagttt taccacttat ttttttataa    60
caccttggta attttgacat taggtagcaa tataatacga taaaattcac ctccatgtaa  120
tttgaagttc ttttcaataa ttttttgac aaattttata gaagaattta acctttttt   180 ttttggttca aacgaagaaa tgtttccgtc attcaattaa aattaatgac atcatctagt  240
ggctcggtga catacgcttt agatacaatt gtcattcttg cctttttcctt tctctatata  300 aacccctttt gccttgaact tgtttcaac taaagcagct cctcctcatc ccttactgtc   360
tttgctttct cactaactac tacaacccaa cagttttctt ctctcaaaa              409

<210> SEQ ID NO 110
<211> LENGTH: 409
<212> TYPE: DNA
<213> ORGANISM: Citrus paradisi

<400> SEQUENCE: 110
attcatatta acgttatcaa tgatttttta aaatagttt taccactttt ttttttataa    60
caccttggta attttgacat taggtagcaa tataatacga taaaattcac ctccatgtaa  120

-continued

```
tttgaagttc ttttcaataa ttttttgac aaattttata gaagaattta accttttctt    180 ttttttttc aaacgaagaa atgttttcgt cattcaatta aaattaatga catcatctag    240
tggcttggtg acatacgctt tagatacgat tgtcattctt gccttttcct ttctctatat    300 aaacccctt tgccttaact ttgtttcaac taaagcagct cctcctcatc ccttactgtc    360
ttcgctttct cactaactac tacaacccaa cagttttctt ctctcaaaa              409
```